United States Patent
Lee et al.

(10) Patent No.: US 9,957,529 B2
(45) Date of Patent: May 1, 2018

(54) RECOMBINANT MICROORGANISM WITH IMPROVED BUTANOL PRODUCTION ABILITY AND METHOD FOR PRODUCING BUTANOL BY USING THE SAME

(71) Applicant: GS CALTEX CORPORATION, Seoul (KR)

(72) Inventors: Sang-Hyun Lee, Daejeon (KR); Moon-Ho Eom, Daejeon (KR)

(73) Assignee: GS CALTEX CORPORATION, Seoul (KR)

( * ) Notice: Subject to any disclaimer, the term of this patent is extended or adjusted under 35 U.S.C. 154(b) by 0 days. days.

(21) Appl. No.: 14/443,642

(22) PCT Filed: Mar. 11, 2013

(86) PCT No.: PCT/KR2013/001954
§ 371 (c)(1),
(2) Date: May 18, 2015

(87) PCT Pub. No.: WO2014/081084
PCT Pub. Date: May 30, 2014

(65) Prior Publication Data
US 2015/0376655 A1 Dec. 31, 2015

(30) Foreign Application Priority Data
Nov. 20, 2012 (KR) ........................ 10-2012-0131850

(51) Int. Cl.
*C12P 7/16* (2006.01)
*C12N 15/52* (2006.01)

(52) U.S. Cl.
CPC ............... *C12P 7/16* (2013.01); *C12N 15/52* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 1,315,585 A | 9/1919 | Weizmann | |
| 8,039,239 B2 | 10/2011 | Reeves | |
| 9,096,872 B2 * | 8/2015 | Lee | C12N 9/0006 |
| 2009/0155869 A1 | 6/2009 | Buelter et al. | |
| 2013/0017588 A1 * | 1/2013 | Lee | C12N 9/0006 |
| | | | 435/160 |

FOREIGN PATENT DOCUMENTS

| | | |
|---|---|---|
| KR | 1020110033086 A | 3/2011 |
| KR | 1020110033087 A | 3/2011 |
| KR | 1020110033089 A | 3/2011 |
| WO | 2009082148 A2 | 7/2009 |
| WO | 2011037415 A2 | 3/2011 |

OTHER PUBLICATIONS

Inui et al. Appl Microbiol Biotechnol. Jan. 2008;77(6):1305-16. Epub Dec. 1, 2007.*
Lehmann et al. Appl Microbiol Biotechnol. May 2012;94(3):743-54. Epub Jan. 14, 2012.*
Kuit et al. Appl Microbiol Biotechnol. May 2012;94(3):729-41. Epub Jan. 17, 2012.*
Singh et al. Curr Protein Pept Sci. 2017, 18, 1-11.*
Kizer et al. Appl Environ Microbiol. May 2008;74(10):3229-41.*
Prather et al. Curr Opin Biotechnol. Oct. 2008;19(5):468-74.*
Durre, Peter, Biobutanol: An attractive biofuel, Journal, 2007, 1525-1534, vol. 2, Wiley-VCH Verlag GmbH & Co. KGaA, Weinheim.
Takashi Tsuchida et al., Direct Synthesis of n-Butanol from Ethanol over Nonstoichiometric Hydroxyapatite, Article, 2006, 8634-8642, vol. 45, American Chemical Society.
Jin Young Lee et al., Metabolic engineering of Clostridium acetobutylicum M5 for highly selective butanol production, Research Article, 2009, 1432-1440, vol. 4, Wiley-VCH Verlag GmbH & Co. KGaA, Weinheim.
T.C. Ezeji et al., Acetone butanol ethanol (ABE) production from concentrated substrate: reduction in substrate inhibition by fed-batch technique and product inhibition by gas stripping, Paper, 2004, 653-658, vol. 63, Appl Microbiol Biotechnol.
Yu Jiang et al., Disruption of the acetoacetate decarboxylase gene in solvent-producing clostridium acetobutylicum increases the butanol ratio, Article, 2009, 284-291, vol. 11, ELSEVIER.
Lee D. Mermelstein et al., Metabolic Engineering of Clostridium acetobutylicum ATCC 824 for Increased Solvent Production by Enhancement of Acetone Formation Enzyme Activities Using a Synthetic Acetone Operon, 1993, 1053-1060, vol. 42, John Wiley & Sons, Inc.
Edward M. Green et al., Genetic manipulation of acid formation pathways by gene inactivation in Clostridium acetobutylicum ATCC 824, 1996, 2079-2086, vol. 142, Microbiology.
Yu-Sin Jang et al., Enhanced Butanol Production Obtained by Reinforcing the Direct Butanol-Forming Route in Clostridium acetobutylicum, Research Article, 2012, 1-5, vol. 3, Issue 5, mbio.asm.org.
International Search Report for PCT/KR2013/001954 dated Jul. 29, 2013.

* cited by examiner

*Primary Examiner* — Christian Fronda
(74) *Attorney, Agent, or Firm* — Hauptman Ham, LLP

(57) ABSTRACT

The present invention relates to a recombinant microorganism with improved butanol production ability which has an acetyl-CoA synthesis pathway and a butyryl-CoA synthesis pathway, wherein a pathway converting acetyl-CoA to acetate is inhibited and a pathway converting acetyl-CoA to butyryl-CoA is promoted. In addition, the present invention relates to a method for producing butanol using the recombinant microorganism.

16 Claims, 10 Drawing Sheets

Fig. 5

```
                        SEQUENCE LISTING

<160> NUMBER OF SEQ ID NOS: 14

<210> SEQ ID NO 1
<211> LENGTH: 1185
<212> TYPE: DNA
<213> ORGANISM: Clostridium acetobutylicum

<400> SEQUENCE: 1
atgaaaaatt gtgtcatcgt cagtgcggta cgtactgcta tcggtagttt taacggttca      60
ctcgcttcca ccagcgccat cgacctgggg gcgacagtaa ttaaagccgc cattgaacgt     120
gcaaaaatcg attcacaaca cgttgatgaa gtgattatgg gtaacgtgtt acaagccggg     180 ctgggcaaa atccggcgcg tcaggcactg ttaaaaagcg ggctggcaga acggtgtgc      240 ggattcacgg tcaataaagt atgtggttcg ggtcttaaaa gtgtggcgct tgccgcccag     300
gccattcagg caggtcaggc gcagagcatt gtggcggggg gtatggaaaa tatgagttta     360 gcccctact tactcgatgc aaaagcacgc tctggttatc gtcttggaga cggacaggtt     420
tatgacgtaa tcctgcgcga tggcctgatg tgcgccaccc atggttatca tatggggatt     480
accgccgaaa acgtggctaa agagtacgga attacccgtg aaatgcagga tgaactggcg     540
ctacattcac agcgtaaagc ggcagccgca attgagtccg gtgcttttac agccgaaatc     600
gtcccggtaa atgttgtcac tcgaaagaaa accttcgtct tcagtcaaga cgaattcccg     660
aaagcgaatt caacggctga agcgttaggt gcattgcgcc cggccttcga taaagcagga     720
acagtcaccg ctgggaacgc gtctggtatt aacgacggtg ctgccgctct ggtgattatg     780
gaagaatctg cggcgctggc agcaggcctt accccctgg ctcgcattaa aagttatgcc     840
agcggtggcg tgccccccgc attgatgggt atggggccag tacctgccac gcaaaaagcg     900
ttacaactgg cggggctgca actggcggat attgatctca ttgaggctaa tgaagcattt     960
gctgcacagt tccttgccgt tgggaaaaac ctgggctttg attctgagaa agtgaatgtc    1020
aacggcgggg ccatcgcgct cggcatcct atcggtgcca gtggtgctcg tattctggtc    1080
acactattac atgccatgca ggcacgcgat aaaacgctgg ggctggcaac actgtgcatt    1140
ggcggcggtc agggaattgc gatggtgatt gaacggttga attaa                   1185

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 2
atactgcaga tgaaaaattg tgtcatcgtc agtgcgg                              37

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atactcgagt taattcaacc gttcaatcac catc                                 34

<210> SEQ ID NO 4
<211> LENGTH: 4759
<212> TYPE: DNA
<213> ORGANISM: Clostridium acetobutylicum

<400> SEQUENCE: 4
atggaactaa caatgtcat ccttgaaaag gaaggtaaag ttgctgtagt taccattaac      60
agacctaaag cattaaatgc gttaaatagt gatacactaa agaaatgga ttatgttata    120 ggtgaaattg aaaatgatag cgaagtactt gcagtaattt taactggagc aggagaaaaa    180
tcatttgtag caggagcaga tatttctgag atgaaggaaa tgaataccat gaaggtaga    240 aaattcggga tacttggaaa taaagtgttt agaagattag aacttcttga aaagcctgta    300
atagcagctg ttaatggttt tgctttagga ggcggatgcg aaatagctat gtcttgtgat    360
ataagaatag cttcaagcaa cgcaagattt ggtcaaccag aagtaggtct cggaataaca    420
cctggttttg gtggtacaca aagactttca agattagttg gaatgggcat ggcaaagcag    480
cttatattta ctgcacaaaa tataaaggca gatgaagcat taagaatcgg acttgtaaat    540
aaggtagtag aacctagtga attaatgaat acagcaaaag aaattgcaaa caaaattgtg    600
agcaatgctc cagtagctgt taagttaagc aaacaggcta ttaatagagg aatgcagtgt    660
gatattgata ctgctttagc atttgaatca gaagcatttg gagaatgctt ttcaacagag    720
gatcaaaagg atgcaatgac agctttcata gagaaaagaa aaattgaagg cttcaaaaat    780
agataggagg taagtttata tggattttaa tttaacaaga gaacaagaat tagtaagaca    840
gatggttaga gaatttgctg aaaatgaagt taaacctata gcagcagaaa ttgatgaaac    900
agaaagattt ccaatggaaa atgtaaagaa atgggtcag tatggtatga tgggaattcc    960
attttcaaaa gagtatggtg cgcaggtgg agatgtatta tcttatataa tcgccgttga   1020
ggaattatca aaggtttgcg gtactacagg agttattctt tcagcacata catcactttg   1080
tgcttcatta ataaatgaac atggtacaga agaacaaaaa caaaatatt tagtaccttt   1140 agctaaaggt gaaaaatag gtgcttatgg attgactgag ccaaatgcag gaacagattc   1200
tggagcacaa caaacagtag ctgtacttga aggagatcat tatgtaatta atggttcaaa   1260
aatattcata actaatggag gagttgcaga tacttttgtt atatttgcaa tgactgacag   1320
aactaaagga acaaaaggta tatcagcatt tataatagaa aaaggcttca aaggtttctc   1380
tattggtaaa gttgaacaaa agcttggaat aagagcttca tcaacaactg aacttgtatt   1440
tgaagatatg atagtaccag tagaaaacat gattggtaaa gaaggaaaag gcttcccctat   1500 agcaatgaaa actcttgatg gaggaagaat tggtatagca gctcaagctt aggtatagc   1560 tgaaggtgct ttcaacgaag caagagctta catgaaggag agaaaacaat ttggaagaag   1620
```

```
ccttgacaaa ttccaaggtc ttgcatggat gatggcagat atggatgtag ctatagaatc    1680
agctagatat ttagtatata aagcagcata tcttaaacaa gcaggacttc catacacagt    1740
tgatgctgca agagctaagc ttcatgctgc aaatgtagca atggatgtaa caactaaggc    1800
agtacaatta tttggtggat acggatatac aaaagattat ccagttgaaa gaatgatgag    1860
agatgctaag ataactgaaa tatatgaagg aacttcagaa gttcagaaat tagttatttc    1920
aggaaaaatt tttagataat ttaaggaggt taagaggatg aatatagttg tttgtttaaa    1980
acaagttcca gatacagcgg aagttagaat agatccagtt aagggaacac ttataagaga    2040
aggagttcca tcaataataa atccagatga taaaaacgca cttgaggaag ctttagtatt    2100
aaaagataat tatggtgcac atgtaacagt tataagtatg ggacctccac aagctaaaaa    2160
tgctttagta gaagctttgg ctatgggtgc tgatgaagct gtacttttaa cagatagagc    2220
atttggagga gcagatacac ttgcgacttc acatacaatt gcagcaggaa ttaagaagct    2280
aaaatatgat atagttttg ctggaaggca ggctatagat ggagatacag ctcaggttgg    2340
accagaaata gctgagcatc ttggaatacc tcaagtaact tatgttgaga aagttgaagt    2400
tgatggagat actttaaaga ttagaaaagc ttgggaagat ggatatgaag ttgttgaagt    2460
taagacacca gttcttttaa cagcaattaa agaattaaat gttccaagat atatgagtgt    2520
agaaaaaata ttcggagcat ttgataaaga agtaaaaatg tggactgccg atgatataga    2580
tgtagataag gctaatttag gtcttaaagg ttcaccaact aaagttaaga agtcatcaac    2640
taaagaagtt aaaggacagg gagaagttat tgataagcct gttaaggaag cagctgatat    2700
gttgtctcaa aattaaaaga agaacacata tttaagttag gagggattt tcaatgaata    2760 aagcagatta caagggcgta tgggtgtttg ctgaacaaag agacggagaa ttacaaaagg    2820
tatcattgga attattaggt aaaggtaagg aaatggctga gaaattaggc gttgaattaa    2880
cagctgtttt acttggacat aatactgaaa aaatgtcaaa ggatttatta tctcatggag    2940
cagataaggt tttagcagca gataatgaac ttttagcaca tttttcaaca gatggatatg    3000
ctaaagttat atgtgattta gttaatgaaa gaaagccaga aatattattc ataggagcta    3060 cttttcatagg aagagattta ggaccaagaa tagcagcaag actttctact ggtttaactg    3120
ctgattgtac atcacttgac atagatgtag aaaatagaga tttattggct acaagaccag    3180 cgttggtgg aaatttgata gctacaatag tttgttcaga ccacagacca caaatggcta    3240
cagtaagacc tggtgtgttt tttgaaaaat tacctgttaa tgatgcaaat gtttctgatg    3300
ataaaataga aaaagttgca attaaattaa cagcatcaga cataagaaca aaagtttcaa    3360
aagttgttaa gcttgctaaa gatattgcag atatcggaga agctaaggta ttagttgctg    3420
gtggtagagt agttggaagc aaagaaaact ttgaaaaact tgaagagtta gcaagtttac    3480
ttggtggaac aatagccgct tcaagagcag caatagaaaa agaatgggtt gataaggacc    3540
ttcaagtagg tcaaactggt aaaactgtaa gaccaactct ttatattgca tgtggtatat    3600
caggagctat ccagcattta gcaggtatgc aagattcaga ttacataatt gctataaata    3660
aagatgtaga agccccaata atgaaggtag cagatttggc tatagttggt gatgtaaata    3720
aagttgtacc agaattaata gctcaagtta aagctgctaa taattaagat aaataaaaag    3780
aattatttaa agcttattat gccaaaatac ttatatagta ttttggtgta aatgcattga    3840
tagtttcttt aaatttaggg aggtctgttt aatgcattga tagttcttta aatttaggga    3900
ggtctgttta atgaaaaagg tatgtgttat aggtgcaggg actatgggtt caggaattgc    3960
tcaggcattt gcagctaaag gatttgaagt agtattaaga gatattaaag atgaatttgt    4020
```

-continued

```
tgatagagga ttagatttta tcaataaaaa tctttctaaa ttagttaaaa aaggaaagat    4080
agaagaagct actaaagttg aaatcttaac tagaatttcc ggaacagttg accttaatat    4140
ggcagctgat tgcgatttag ttatagaagc agctgttgaa agaatggata ttaaaaagca    4200 gattttttgct gacttagaca atatatgcaa gccagaaaca attcttgcat caaatacatc   4260
atcactttca ataacagaag tggcatcagc aactaaaact aatgataagg ttataggtat    4320 gcatttctttt aatccagctc ctgttatgaa gcttgtagag gtaataagag gaatagctac   4380
atcacaagaa acttttgatg cagttaaaga gacatctata gcaataggaa agatcctgt    4440 agaagtagca gaagcaccag gatttgttgt aaatagaata ttaataccaa tgattaatga   4500
agcagttggt atattagcag aaggaatagc ttcagtagaa gacatagata aagctatgaa   4560
acttggagct aatcacccaa tgggaccatt agaattaggt gattttatag gtcttgatat    4620
atgtcttgct ataatggatg ttttatactc agaaactgga gattctaagt atagaccaca   4680
tacattactt aagaagtatg taagagcagg atggcttgga agaaaatcag gaaaaggttt    4740
ctacgattat tcaaaataa                                                  4759
```

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
atactgcaga tggaactaaa caatgtcatc cttgaaaagg aagg                       44
```

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
atactcgagt tattttgaat aatcgtagaa accttttcct g                          41
```

<210> SEQ ID NO 7
<211> LENGTH: 2589
<212> TYPE: DNA
<213> ORGANISM: Clostridium acetobutylicum

<400> SEQUENCE: 7

```
atgaaagtca acacagtaaa ggaattagat gaaaaactca aggtaattaa agaagctcaa      60
aaaaaattct cttgttactc gcaagaaatg gttgatgaaa tctttagaaa tgcagcaatg    120
gcagcaatcg acgcaaggat agagctagca aaagcagctg ttttggaaac cggtatgggc   180
ttagttgaag acaaggttat aaaaaatcat tttgcaggcg aatacatcta taacaaatat    240
aaggatgaaa aaacctgcgg tataattgaa cgaaatgaac cctacggaat tacaaaaata    300
gcagaaccta taggagttgt agctgctata tccctgtaa caaaccccac atcaacaaca    360
atatttaaat ccttaatatc ccttaaaact agaaatggaa ttttctttttc gcctcaccca    420 agggcaaaaa aatccacaat actagcagct aaaacaatac ttgatgcagc cgttaagagt    480
ggtgccccgg aaaatataat aggttggata gatgaacctt caattgaact aactcaatat    540
```

```
ttaatgcaaa aagcagatat aacccttgca actggtggtc cctcactagt taaatctgct        600
tattcttccg gaaaaccagc aataggtgtt ggtccgggta acaccccagt aataattgat        660
gaatctgctc atataaaaat ggcagtaagt tcaattatat tatccaaaac ctatgataat        720
ggtgttatat gtgcttctga acaatctgta atagtcttaa aatccatata taacaaggta        780
aaagatgagt tccaagaaag aggagcttat ataataaaga aaaacgaatt ggataaagtc        840
cgtgaagtga tttttaaaga tggatccgta aaccctaaaa tagtcggaca gtcagcttat        900
actatagcag ctatggctgg cataaaagta cctaaaacca caagaatatt aataggagaa        960
gttacctcct taggtgaaga agaacctttt gcccacgaaa aactatctcc tgttttggct       1020
atgtatgagg ctgacaattt tgatgatgct ttaaaaaaag cagtaactct aataaactta       1080
ggaggcctcg gccatacctc aggaatatat gcagatgaaa taaaagcacg agataaaata       1140
gatagattta gtagtgccat gaaaaccgta agaaccttg taaatatccc aacctcacaa       1200
ggtgcaagtg gagatctata taattttaga ataccaccct ctttcacgct tggctgcgga       1260
ttttggggag gaaattctgt tccgagaat gttggtccaa acatcttt gaatattaaa        1320 accgtagctg aaaggagaga aaacatgctt tggtttagag ttccacataa agtatatttt       1380
aagttcggtt gtcttcaatt tgcttaaaaa gatttaaaag atctaaagaa aaaaagagcc       1440
tttatagtta ctgatagtga cccctataat ttaaactatg ttgattcaat aataaaaata       1500
cttgagcacc tagatattga tttaaagta tttaataagg ttggaagaga agctgatctt       1560
aaaaccataa aaaagcaac tgaagaaatg tcctccttta tgccagacac tataatagct       1620
ttaggtggta cccctgaaat gagctctgca aagctaatgt gggtactata tgaacatcca       1680
gaagtaaaat ttgaagatct tgcaataaaa tttatggaca taagaaagag aatatatact       1740
ttcccaaaac tcggtaaaaa ggctatgtta gttgcaatta caactctgc tggtccgt      1800 tctgaggtta ctccttttgc tttagtaact gacaataaca ctggaaataa gtacatgtta       1860
gcagattatg aaatgacacc aaatatggca attgtagatg cagaactat gatgaaaatg       1920 ccaaagggat taaccgctta ttcaggtata gatgcactag taaatagtat agaagcatac       1980
acatccgtat atgcttcaga atacacaaac ggactagcac tagaggcaat acgattaata       2040
tttaaatatt tgcctgaggc ttacaaaaac ggaagaacca atgaaaaagc aagagagaaa       2100
atggctcacg cttcaactat ggcaggtatg gcatccgcta atgcattct aggtctatgt       2160 cattccatgg caataaaatt aagttcagaa cacaatattc ctagtggcat tgccaatgca       2220
ttactaatag aagaagtaat aaaatttaac gcagttgata tcctgtaaaa caagccct       2280 tgcccacaat ataagtatcc aaacaccata tttagatatg ctcgaattgc agattatata       2340
aagcttggag gaaatactga tgaggaaaag gtagatctct taattaacaa aatacatgaa       2400 ctaaaaaag ctttaaatat accaacttca ataaggatg caggtgtttt ggaggaaaac       2460
ttctattcct ccccttgatag aatatctgaa cttgcactag atgatcaatg cacaggcgct       2520
aatcctagat ttcctcttac aagtgagata aagaaatgt atataaattg ttttaaaaa        2580 caaccttaa                                                              2589
```

<210> SEQ ID NO 8  
<211> LENGTH: 39  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 8
cacctgcaga tgaaagtcac aacagtaaag gaattagat                                39

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cacctcgagt taaggttgtt ttttaaaaca atttatatac a                             41

<210> SEQ ID NO 10
<211> LENGTH: 1537
<212> TYPE: DNA
<213> ORGANISM: Clostridium acetobutylicum

<400> SEQUENCE: 10

| | |
|---|---|
| accttcatat ttcaactact ttttataatt ttaataaaga atttaaaagg agggattaaa | 60 |
| atgaactcta aaataattag atttgaaaat ttaaggtcat tctttaaaga tgggatgaca | 120 |
| attatgattg gaggtttttt aaactgtggc actccaacca aattaattga tttttttagtt | 180 |
| aatttaaata taaagaattt aacgattata agtaatgata catgttatcc taatacaggt | 240 |
| attggtaagt taatatcaaa taatcaagta aaaaagctta ttgcttcata tataggcagc | 300 |
| aacccagata ctggcaaaaa acttttttaat aatgaacttg aagtagagct ctctccccaa | 360 |
| ggaactctag tggaaagaat acgtgcaggc ggatctggct taggtggtgt actaactaaa | 420 |
| acaggtttag gaactttgat tgaaaaagga agaaaaaaa tatctataaa tggaacggaa | 480 |
| tatttgttag agctacctct tacagccgat gtagcattaa ttaaaggtag tattgtagat | 540 |
| gaggccggaa acaccttcta taaggtact actaaaaact ttaatcccta tatggcaatg | 600 |
| gcagctaaaa ccgtaatagt tgaagctgaa aatttagtta gctgtgaaaa actagaaaag | 660 |
| gaaaaagcaa tgaccccccgg agttcttata aattatatag taaaggagcc tgcataaaat | 720 |
| gattaatgat aaaaaacctag cgaaagaaat aatagccaaa agagttgcaa gagaattaaa | 780 |
| aaatggtcaa cttgtaaact taggtgtagg tcttcctacc atggttgcag attatatacc | 840 |
| aaaaaatttc aaaattactt tccaatcaga aaacggaata gttggaatgg gcgctagtcc | 900 |
| taaaataaat gaggcagata agatgtagt aaatgcagga ggagactata aacagtact | 960 |
| tcctgacggc acatttttcg atagctcagt ttcgttttca ctaatccgtg gtggtcacgt | 1020 |
| agatgttact gttttagggg ctctccaggt agatgaaaag ggtaatatag ccaattggat | 1080 |
| tgttcctgga aaaatgctct ctggtatggg tggagctatg gatttagtaa atggagctaa | 1140 |
| gaaagtaata attgcaatga gacatacaaa taaaggtcaa cctaaaattt taaaaaaatg | 1200 |
| tacacttccc ctcacggcaa agtctcaagc aaatctaatt gtaacagaac ttggagtaat | 1260 |
| tgaggttatt aatgatggtt tacttctcac tgaaattaat aaaaacacaa ccattgatga | 1320 |
| aataaggtct ttaactgctg cagatttact catatccaat gaacttagac ccatggctgt | 1380 |
| ttagaaagaa atactatgaa acaatattaa aaaaataaga gttaccattt aaggtaactc | 1440 |
| ttattttttat tacttaagat aatcatatat aacttcagct ctaggcaata ttatatctgc | 1500 |
| aagaatgtga gagctagaaa caatctcttt tactggc | 1537 |

<210> SEQ ID NO 11

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cacctcgaga ccttcatatt tcaactactt tttat                              35

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tacgcgtcga cgccagtaaa agagattgtt tctagc                             36

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atagtcgaca tgaagtttct tatgcacaag tatttttat tacattaa                 48

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taagttgggt aacgccaggg                                               20
```

RECOMBINANT MICROORGANISM WITH IMPROVED BUTANOL PRODUCTION ABILITY AND METHOD FOR PRODUCING BUTANOL BY USING THE SAME

CROSS REFERENCE TO RELATED APPLICATION

This application claims the priority of Korean Patent Application No. 10-2012-0131850 filed on Nov. 20, 2012 in the Korean Patent and Trademark Office. Further, this application is the National Phase application of International Application No. PCT/KR2013/001954 filed on Mar. 11, 2013, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 20, 2015, is named 5230-0469_SL.txt and is 16,251 bytes in size.

TECHNICAL FIELD

The present invention relates to a recombinant microorganism with improved butanol production ability and a method for producing butanol using the same.

BACKGROUND ART

Butanol is an intermediate compound with a wide range of applications such as cosmetics, perfumes, hormones, sanitary agents, industrial coating agents, additives for paints, fibers, plastic monomers, medicinal products, vitamins, antibiotics, pesticides, and the like, and thus considered to be very useful (Durre, Biotechnol J., 2:1525-1534, 2007).

As a prior method for producing butanol, a method for producing butanol, acetone and ethanol by fermenting sugars using Clostridium strains (Weizmann, U.S. Pat. No. 1,315,585) was utilized until the 1980's. After that, an oxo process of synthesizing butanol from propylene obtained from petroleum has been widely utilized. However, such a petroleum-based method for producing butanol has drawbacks in that the production process is complex due to employment of high pressures and high temperatures, and that a large amount of hazardous waste and carbon dioxide are discharged from the method (Tsuchida et al., Ind. Eng. Chem. Res., 45:8634, 2006). In this regard, recently there has been a growing need for an environmentally friendly method for producing butanol through fermentation of renewable sources using microorganisms.

However, in order to produce butanol at an industrial level using microorganisms, butanol selectivity, yield and productivity (namely, produced amount of butanol per hour) should be good. However, wild type or recombinant microorganisms used in the production of biobutanol have to meet such conditions.

Specifically, wild type Clostridium acetobutylicum ATCC 824 is known to produce acetone, ethanol and butanol in a weight ratio of about 3:1:6 through fermentation, wherein a small amount of acetic acid and butyric acid are also produced. The yield of the wild type strain is about 25%, and the final concentration is about 10 g/L. Microorganisms having an acetyl-CoA biosynthetic pathway and a butyryl-CoA biosynthetic pathway, such as Clostridium acetobutylicum, are generally known to synthesize acetone, butanol and ethanol by a pathway depicted in FIG. 1. With the recent development of metabolic engineering technology, continuous efforts have been focused on more effective production of butanol. In particular, in the case of Clostridium acetobutylicum, studies related to metabolic pathway mechanisms are actively carried out as the full genome thereof has recently been sequenced.

For example, test results in which adhE1 (alcohol/aldehyde dehydrogenase) and ctfAB genes are simultaneously overexpressed in a Clostridium acetobutylicum M5 strain that has lost magaplasmid having butanol production related genes (adc, ctfAB, adhE1 (alcohol/aldehyde dehydrogenase) and adhE2 (alcohol/aldehyde dehydrogenase)) were reported. According to the report, butanol selectivity was found to be enhanced to 0.78 in a weight ratio, but there were some limitations in that productivity and yield were greatly decreased due to the inhibited strain growth and increased acetic acid production (Lee, et al., Biotechnol. J., 4:1432-1440, 2009; Lee, et al., WO 2009/082148).

In the case that a pta gene converting acetyl-CoA to acetate was deleted, and in the case that a pta gene and a buk gene converting butyryl-CoA to butyrate were deleted and then an aad gene (alcohol/aldehyde dehydrogenase) was overexpressed, it was reported that butanol concentration, selectivity and yield were increased. However, both cases still had limitations in view of productivity and stability of strains (LEE et al., WO 2011/037415). Further, in the case that the ctfB gene encoding CoA transferase (CoAT) was additionally deleted from the pta and buk deleted mutant, the productivity was still found to be low (LEE et al., WO 2011/037415).

Besides, there has been an example that reports the production of 18.6 g/l of butanol as the result of fermentation by a randomly mutated mutant Clostridium beijerinckii BA101 strain and using maltodextrin as a carbon source (Ezeji et al., Appl. Microbiol. Biotechnol., 63:653, 2004). However, use of the recombinant strains showed low productivity of the final product, butanol, which makes industrial applicability impossible.

Further, there has been an example that reports decrease in acetone concentration and increase in butanol selectivity by deleting the ctfAB gene encoding CoA transferase or the adc (acetoacetic acid decarboxylase) gene. However, this example has problems in that the final concentration of butanol is less than 10 g/L and the strain is not stable (Jiang et al., Metab. Eng., 11(4-5):284-291, 2009).

Furthermore, in the case of overexpressing adc (acetoacetic acid decarboxylase) and ctfAB (CoA transferase) genes in wild type Clostridium acetobutylicum, acetone, ethanol and butanol productivity are reported to be increased to 95%, 90%, and 37%, respectively, as compared to those of the wild type Clostridium acetobutylicum. However, the example has problems in that butanol selectivity and yield are low (Mermelstein et al., Biotechnol. Bioeng., 42:1053, 1993).

In the course of the present inventors' earnest research to find a microorganism having excellent butanol selectivity, yield and productivity, a recombinant microorganism with inhibited phosphotransacetylase and butyrate kinase activity, increased CoA transferase and aldehyde/alcohol dehydrogenase activity, and increased thiolase or hbd-crt-bcd operon activity among the microorganisms having an acetyl-CoA biosynthetic pathway and a butyryl-CoA biosynthetic pathway has been found to exhibit high butanol selectivity and yield with low ethanol selectivity, thereby allowing continuous production of biobutanol on an industrial scale. Based on this finding, the present invention has been accomplished.

DISCLOSURE

Technical Problem

It is an object of the present invention to provide a recombinant microorganism having high butanol selectivity and yield with low ethanol selectivity, allowing the continuous production of biobutanol on an industrial scale.

Technical Solution

In accordance with one aspect of the present invention, there is provided a recombinant microorganism with improved butanol production ability which has an acetyl-CoA biosynthetic pathway and a butyryl-CoA biosynthetic pathway, wherein a pathway converting acetyl-CoA into acetate is inhibited and a pathway converting acetyl-CoA to butyryl-CoA is promoted.

In accordance with another aspect of the present invention, there is provided a method for producing butanol including: culturing the recombinant microorganism according to the present invention; and recovering butanol from the culture solution.

Advantageous Effects

The recombinant microorganism according to the present invention exhibits high ABE (acetone, butanol and ethanol) yield, butanol productivity, and butanol selectivity with low ethanol selectivity. Therefore, the recombinant microorganism according to the present invention is capable of continuously producing biobutanol on industrial scale.

DESCRIPTION OF DRAWINGS

Figure 5:
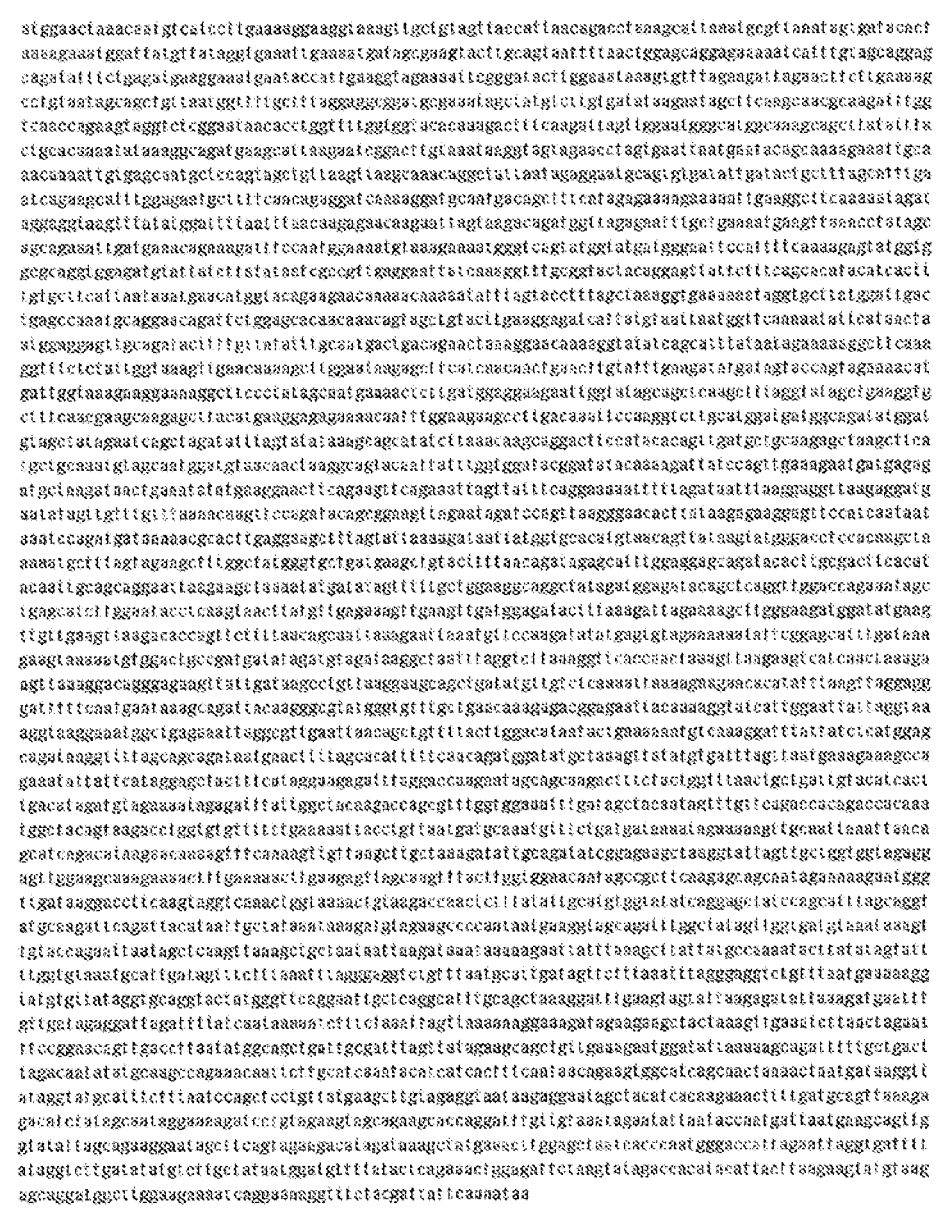

FIG. 5 shows a base sequence of SEQ ID NO: 4.

BEST MODE

The present invention relates to a recombinant microorganism with improved butanol production ability, which has an acetyl-CoA biosynthetic pathway and a butyryl-CoA biosynthetic pathway, wherein a pathway converting acetyl-CoA into acetate is inhibited and a pathway converting acetyl-CoA into butyryl-CoA is promoted.

Further, the present invention relates to a method for producing butanol including: culturing the recombinant microorganism according to the present invention; and recovering butanol from the culture solution.

Hereinafter, the present invention will be described in detail.

The recombinant microorganism according to the present invention is a recombinant microorganism with improved butanol production ability which has an acetyl-CoA biosynthetic pathway and a butyryl-CoA biosynthetic pathway, wherein a pathway converting acetyl-CoA to acetate is inhibited and a pathway converting acetyl-CoA into butyryl-CoA is promoted.

The recombinant microorganism can promote or inhibit other pathways. For example, the recombinant microorganism can promote one or more pathways selected from a pathway converting acetyl-CoA into acetoacetyl-CoA, a pathway converting acetoacetyl-CoA into butyryl-CoA, a pathway converting acetate into acetyl-CoA, a pathway converting butyrate into butyryl-CoA, and a pathway converting butyryl-CoA into butanol. Further, the recombinant microorganism can inhibit a pathway converting butyryl-CoA to butyrate.

Figure 1:
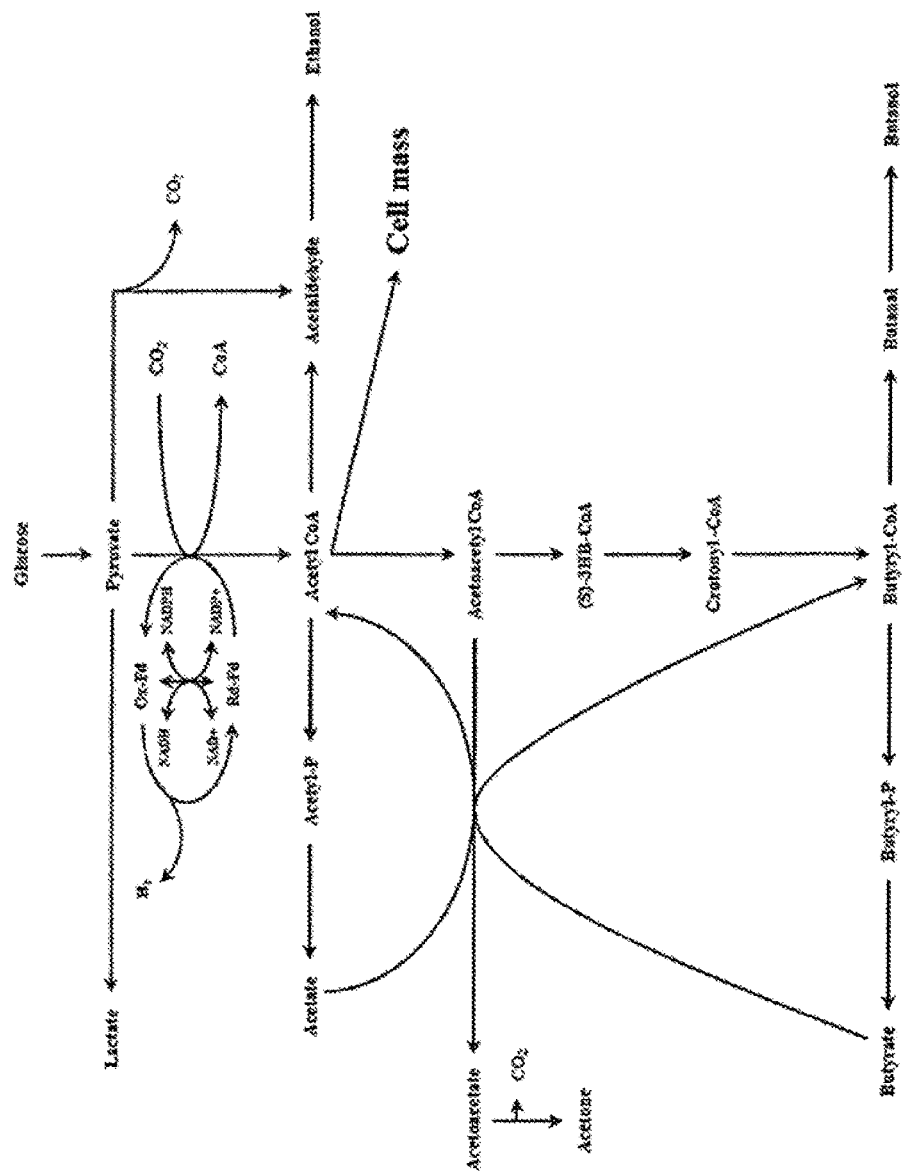
FIG. 1 shows pathways for synthesizing acetone, butanol and ethanol in a microorganism having an acetyl-CoA biosynthetic pathway and a butyryl-CoA biosynthetic pathway.
Figure 2:
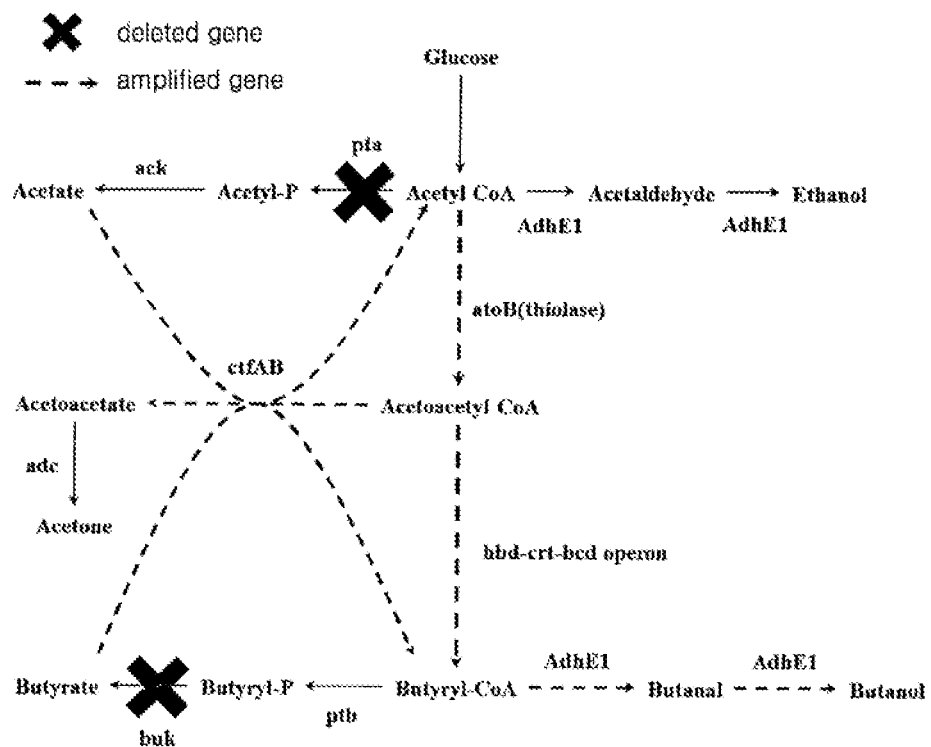
FIG. 2 shows an example of the recombinant microorganism according to the present invention.

Preferably, as shown in FIG. 2, the recombinant microorganism is a recombinant microorganism which has an acetyl-CoA biosynthetic pathway and a butyryl-CoA biosynthetic pathway, wherein both a pathway converting acetyl-CoA into acetate and a pathway converting butyryl-CoA into butyrate are inhibited, and a pathway converting acetyl-CoA into butyryl-CoA, a pathway converting acetate into acetyl-CoA, a pathway converting butyrate into butyryl-CoA and a pathway converting butyryl-CoA into butanol are promoted.

In one embodiment, the recombinant microorganism is a recombinant microorganism having an acetyl-CoA biosynthetic pathway and a butyryl-CoA biosynthetic pathway, wherein phosphotransacetylase and butyrate kinase activities are inhibited, CoA transferase and aldehyde/alcohol dehydrogenase activities are increased, and thiolase or hbd-crt-bcd operon activity is increased.

Acetyl-CoA Biosynthetic Pathway

Herein, the acetyl-CoA biosynthetic pathway refers to a pathway in which acetyl-CoA is synthesized from a specific metabolic product in a microorganism. The acetyl-CoA biosynthetic pathway may be a pathway in which acetyl-CoA is synthesized from pyruvate or a pathway in which acetyl-CoA is synthesized from acetate, and the like. The pathway in which acetyl-CoA is synthesized from acetate may be regulated by CoA transferase.

Butyryl-CoA Biosynthetic Pathway

Herein, the butyryl-CoA biosynthetic pathway refers to a pathway in which butyryl-CoA is synthesized from a specific metabolic product in a microorganism. The butyryl-CoA biosynthetic pathway may be a pathway in which butyryl-CoA is synthesized from acetyl-CoA, a pathway in which butyryl-CoA is synthesized from acetoacetyl-CoA, or a pathway in which butyryl-CoA is synthesized from butyrate, and the like. The pathway in which butyryl-CoA is synthesized from butyrate may be regulated by CoA transferase.

Microorganism Having Acetyl-CoA Biosynthetic Pathway and Butyryl-CoA Biosynthetic Pathway Microorganisms having the acetyl-CoA biosynthetic pathway and the butyryl-CoA biosynthetic pathway are not particularly limited so long as microorganisms have those biosynthetic pathways. Further, the microorganism according to the present invention may be a wild type microorganism having the acetyl-CoA biosynthetic pathway and the butyryl-CoA biosynthetic pathway or a recombinant microorganism having the acetyl-CoA biosynthetic pathway and the butyryl-CoA biosynthetic pathway through genetic recombination. Preferably, the microorganism according to the present invention is *Clostridium* without being limited thereto.

Inhibition of Pathway Converting Acetyl-CoA to Acetate

The biosynthesized acetyl-CoA may be converted to acetate via acetyl phosphate. The pathway may be inhibited by regulating the step of converting acetyl-CoA into acetyl-phosphate or the step of converting acetyl-phosphate into acetate. Those steps may be inhibited by known methods such as expression regulation of enzymes regulating each step or inhibition of enzyme activity.

For example, phosphotransacetylase regulates conversion of acetyl-CoA to acetyl-phosphate. The pathway converting acetyl-CoA into acetate may be inhibited by inhibiting phosphotransacetylase. The inhibition of phosphotransacetylase may be performed by inhibiting expression and enzyme activity of phosphotransacetylase, and the like. For example, those skilled in the art can inhibit phosphotransacetylase by selecting an appropriate method such as deleting a pta gene encoding phosphotransacetylase, causing mutations in the pta gene (mutations such as inhibition of normal gene expression of genes through changing, substituting or deleting a part of the base sequence or introducing a part of the base sequence), regulating gene expression in the course of transcription or translation procedures, and the like.

Further, acetate kinase (ack) regulates conversion of acetyl phosphate into acetate. The pathway converting acetyl-CoA into acetate may be inhibited by inhibiting acetate kinase. The inhibition of acetate kinase may be performed by inhibiting expression and enzyme activity of acetate kinase, and the like. For example, those skilled in the art can inhibit acetate kinase by selecting an appropriate method such as deleting an ack gene encoding acetate kinase, causing mutations in the ack gene (mutations such as inhibition of normal gene expression of genes through changing, substituting or deleting a part of the base sequence or introducing a part of the base sequence), regulating gene expression in the course of transcription or translation procedures, and the like.

Inhibition of Pathway Converting Butyryl-CoA into Butyrate

The biosynthesized butyryl-CoA may be converted into butyrate via butyryl phosphate. The pathway may be inhibited by regulating the step of converting butyryl-CoA into butyryl-phosphate or the step of converting butyryl-phosphate into butyrate. Those steps may be inhibited by known methods such as expression regulation of enzymes regulating each step or inhibition of enzyme activity.

For example, butyrate kinase regulates conversion of butyryl phosphate to butyrate. The pathway converting butyryl-CoA to butyrate may be inhibited by inhibiting butyrate kinase. The inhibition of butyrate kinase may be performed by inhibiting expression and enzyme activity of butyrate kinase, and the like. For example, those skilled in the art can inhibit butyrate kinase by selecting an appropriate method such as deleting a buk gene encoding butyrate kinase, causing mutations in the buk gene (mutations such as inhibition of normal gene expression of genes through changing, substituting or deleting a part of the base sequence or introducing a part of the base sequence), regulating gene expression in the course of transcription or translation procedures, and the like.

Further, phosphotransbutylase regulates conversion of butyryl-CoA to butyryl-phosphate. The pathway converting acetyl-CoA to acetate may be inhibited by inhibiting phosphotransbutylase. The inhibition of phosphotransbutylase may be performed by inhibiting expression and enzyme activity of phosphotransbutylase, and the like. For example, those skilled in the art can inhibit acetate kinase by selecting an appropriate method such as deleting a ptb gene encoding the phosphotransbutylase, causing mutations in the ptb gene (mutations such as inhibition of normal gene expression of genes by changing, substituting or deleting a part of the base sequence or introducing a part of the base sequence), regulating gene expression in the course of transcription or translation, and the like.

Acceleration of Pathway Converting Butyrate to Butyryl-CoA

CoA transferase regulates conversion of butyrate to butyryl-CoA. The pathway converting butyrate to butyryl-CoA may be accelerated by increasing the activity of CoA transferase. Increase in the activity of CoA transferase may be performed by increasing expression and enzyme activity of CoA transferase, and the like. For example, those skilled in the art can increase CoA transferase activity by selecting an appropriate method such as introduction, amplification, rearrangement of cftA or ctfB (hereinafter referred to as "ctfAB") gene encoding CoA transferase, or regulation of gene expression in the course of transcription or translation, and the like.

Acceleration of Pathway Converting Acetate to Acetyl-CoA

CoA transferase regulates conversion of acetate to acetyl-CoA. The pathway converting acetate to acetyl-CoA may be accelerated by increasing the activity of CoA transferase. Increase in the activity of CoA transferase may be performed by increasing expression and enzyme activity of CoA transferase and the like. For example, those skilled in the art can increase CoA transferase activity by selecting an appropriate method such as introduction, amplification, rearrangement of ctfAB gene encoding CoA transferase, or regulation of gene expression in the course of transcription or translation, and the like.

CoA transferase also regulates the pathway converting acetoacetyl-CoA to acetoacetate. Therefore, in the case that activity of CoA transferase is increased, the pathway converting acetoacetyl-CoA to acetone via acetoacetate may also be affected. However, the recombinant microorganism according to the present invention shows that other pathways such as a pathway converting acetyl-CoA to butyryl-CoA and the like, and enzymes related to such pathways are appropriately regulated regardless of increase of CoA transferase activity. As a result, acetone production ability is not increased to the extent that performance as a butanol producing strain is significantly inhibited.

Acceleration of Pathway Converting Butyryl-CoA to Butanol

The synthesized butyryl-CoA may be converted to butanol via butanal. The pathway may be accelerated by promoting the step of converting butyryl-CoA to butanal or the step of converting butanal to butanol. Each step may be accelerated by utilizing a known method such as increasing enzyme activity.

For example, aldehyde/alcohol dehydrogenase regulates conversion of butyryl-CoA to butanal and conversion of butanal to butanol. The pathway converting butyryl-CoA to butanol may be accelerated by increasing aldehyde/alcohol dehydrogenase activity. Increase of aldehyde/alcohol dehydrogenase activity may be performed by increasing expression and enzyme activity of aldehyde/alcohol dehydrogenase, and the like. For example, those skilled in the art can increase aldehyde/alcohol dehydrogenase activity by selecting an appropriate method such as introduction, amplification, rearrangement of adhE gene encoding aldehyde/alcohol dehydrogenase, or regulation of gene expression in the course of transcription or translation, and the like.

Aldehyde/alcohol dehydrogenase also regulates the pathway converting acetyl-CoA to ethanol. Therefore, in the case that aldehyde/alcohol dehydrogenase activity is increased, the pathway converting acetyl-CoA to ethanol via acetoaldehyde may also be affected. However, the recombinant microorganism according to the present invention shows that other pathways such as a pathway converting acetyl-CoA to butyryl-CoA and the like, and enzymes related to such pathways are appropriately regulated, regardless of increase of aldehyde/alcohol dehydrogenase activity. As a result, ethanol production ability and ethanol selectivity are decreased.

Acceleration of Pathway Converting Acetyl-CoA to Butyryl-CoA

The synthesized acetyl-CoA may be converted to butyryl-CoA via acetoacetyl-CoA. The pathway may be accelerated by promoting the step of converting acetyl-CoA to acetoacetyl-CoA or the step of converting acetoacetyl-CoA to butyryl-CoA. Each step may be performed by increasing expression and activity of enzymes that regulates each step.

Acceleration of Pathway Converting Acetyl-CoA to Acetoacetyl-CoA

Thiolase regulates conversion of acetyl-CoA to acetoacetyl-CoA. The pathway converting acetyl-CoA to acetoacetyl-CoA may be accelerated by increasing thiolase activity. The increase in thiolase activity may be performed by increasing expression and enzyme activity of thiolase, and the like. For example, those skilled in the art can increase thiolase activity by selecting an appropriate method such as introduction, amplification, rearrangement of atoB gene encoding thiolase, or regulation of gene expression in the course of transcription or translation, and the like.

Acceleration of Pathway Converting Acetoacetyl-CoA to Butyryl-CoA hbd-crt-bcd operon regulates conversion of acetoacetyl-CoA to butyryl-CoA. The pathway converting acetoacetyl-CoA to butyryl-CoA may be accelerated by increasing activity of hbd-crt-bcd operon. The increase in activity of hbd-crt-bcd operon may be performed by increasing gene expression and enzyme activity of hbd-crt-bcd operon, and the like. For example, those skilled in the art can increase hbd-crt-bcd operon activity by selecting an appropriate method such as introduction, amplification, rearrangement of hbd-crt-bcd operon gene, or regulation of gene expression in the course of transcription or translation, and the like.

Improvement of Butanol Production Ability

Improvement of butanol production ability refers to enhancement in view of butanol selectivity (proportion of butanol among produced ABE), butanol productivity (amount of butanol produced per hour) and ABE production yield (the amount of produced ABE with respect to the amount of carbon source consumed in the production) (hereinafter referred to as "yield"). Preferably, improvement of butanol production ability means that butanol selectivity becomes 70% or more, butanol productivity becomes 1.0 g/L/h or more, or yield becomes 28% or more, on a batch culture basis.

Decrease in Ethanol Production Ability

In order to produce biobutanol persistently and continuously on industrial scale, ethanol concentration in a culture solution should be less than a certain level. High ethanol concentration may give rise to toxicity to microorganisms, which makes persistent cultivation difficult and thereby reduces efficiency of the cultivation process. The recombinant microorganism according to the present invention exhibits improved butanol production ability but reduced ethanol production ability.

Decrease in ethanol production ability refers to reduction of ethanol proportion in the produced ABE, namely decrease in ethanol selectivity. Preferably, decrease in ethanol production ability means that ethanol selectivity is 15% or less on a batch culture or fed-batch culture basis. The decrease in ethanol production ability means that ethanol selectivity is 20% or less on a continuous culture basis.

Method for Producing Butanol

The method for producing butanol according to the present invention includes culturing the recombinant microorganism according to the present invention; and recovering butanol from the culture solution.

The culturing step may be any culture method generally used in the process for producing alcohols using microorganisms, without being particularly limited thereto. For example, the culture method according to the present invention may be liquid cultivation or solid cultivation, or batch culture, continuous culture or fed-batch culture, without being particularly limited thereto. Those skilled in the art could easily select an appropriate culture method and perform the present invention.

The method for recovering butanol is any method generally employed in recovery of bioalcohols, and is not particularly limited. For example, the step of recovering butanol according to the present invention may be performed by separation membranes, distillation, or the like. Further, the steps of culturing microorganisms and recovering butanol may be performed simultaneously or sequentially. For example, butanol may be recovered while continuously culturing microorganisms.

MODE FOR INVENTION

The above and other aspects, features, and advantages of the present invention will become apparent from the detailed description of the following embodiments in conjunction with the accompanying drawings. However, it should be understood that the present invention is not limited to the following embodiments and may be embodied in different ways, and that the embodiments are provided for complete disclosure and thorough understanding of the invention by those skilled in the art. The scope of the invention should be defined only by the accompanying claims and equivalents thereof.

Materials and Methods

A gene deleted strain *Clostridium acetobutylicum* PJC4BK Δbuk::MLS'* is the strain reported in the Journal of Microbiology (E M Green et al., 142, pp 2079) in 1996; *Clostridium acetobutylicum* ATCC824 Δpta and *Clostridium acetobutylicum* ATCC824 Δpta Δbuk are constructed in accordance with the method disclosed in WO2011/037415.

On evaluating biobutanol production ability of the recombinant *C. acetobutylicum* strain, alcohol selectivity (proportion of a specific alcohol in the produced mixed solvent (ABE: acetone, butanol, ethanol)), butanol productivity and yield are calculated as below:

Butanol selectivity (%): produced amount of butanol (g)/produced amount of ABE (g)×100

Ethanol selectivity (%): produced amount of ethanol (g)/produced amount of ABE (g)×100

Butanol productivity (g/L/h): amount of butanol produced per unit volume per hour (Butanol productivity in batch culture and fed-batch culture method is based on exponential phase. In continuous culture, butanol productivity is based on cumulative amount of ABE produced in total phase.)

Yield (%): produced amount of ABE (g)/carbon source (g)×100

ABE productivity (g/L/h): amount of ABE produced per hour per unit volume

<Experimental Example 1> Construction of Recombinant Plasmid

Construction of pGS1-atoB

First of all, *E. coli* W3110 was streaked on solid LB medium, followed by aerobic culturing for 24 hours. A colony selected from the streaked solid medium was cultured in 3 ml of a liquid culture medium for 18 hours, followed by centrifuging the culture solution to obtain cells. The cells were washed with 10 ml Tris buffer, followed by purification using a Wizard Genomic DNA Purification Kit (manufactured by Promega Corp., USA) to isolate chromosome of the strain.

atoB gene (SEQ ID NO: 1) was amplified using primers atoB-UP-PstI (SEQ ID NO: 2) and atoB-DN-XhoI (SEQ ID NO: 3) and using the isolated chromosome as a template (Table 1). 100 µl of PCR mixture includes 250 µM dNTP, 20 pmol of each primer, 1.5 mM $MgCl_2$, 10 µl of 10× buffer, 100 ng of DNA template, and 1 unit of pfu polymerase. In PCR, the reaction was repeated for 25 cycles consisting of initial denaturing at 95° C. for 5 minutes, followed by denaturing at 95° C. for 1 minute, annealing at 50° C. for 1 minute and then polymerizing at 72° C. for 1 minute.

Figure 3:
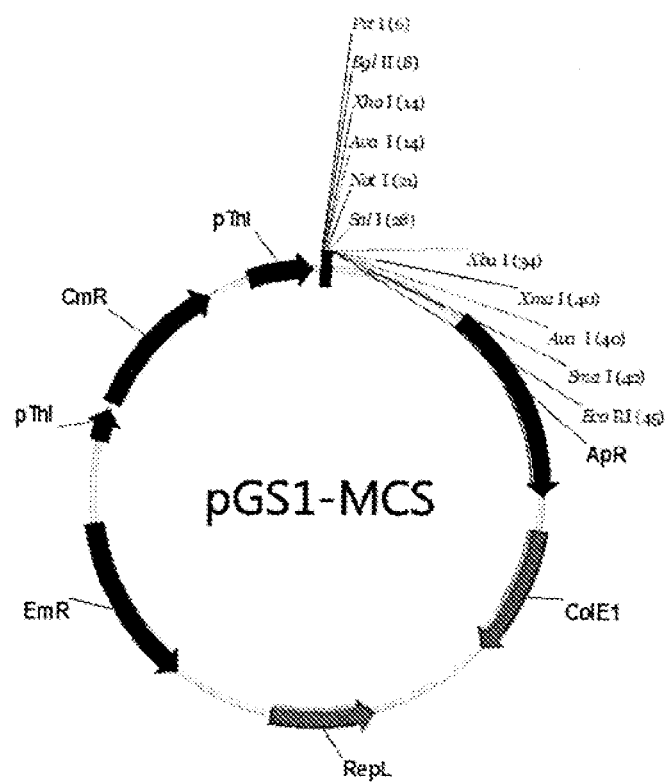
FIG. 3 shows a pGS1-MCS vector.
Figure 4:
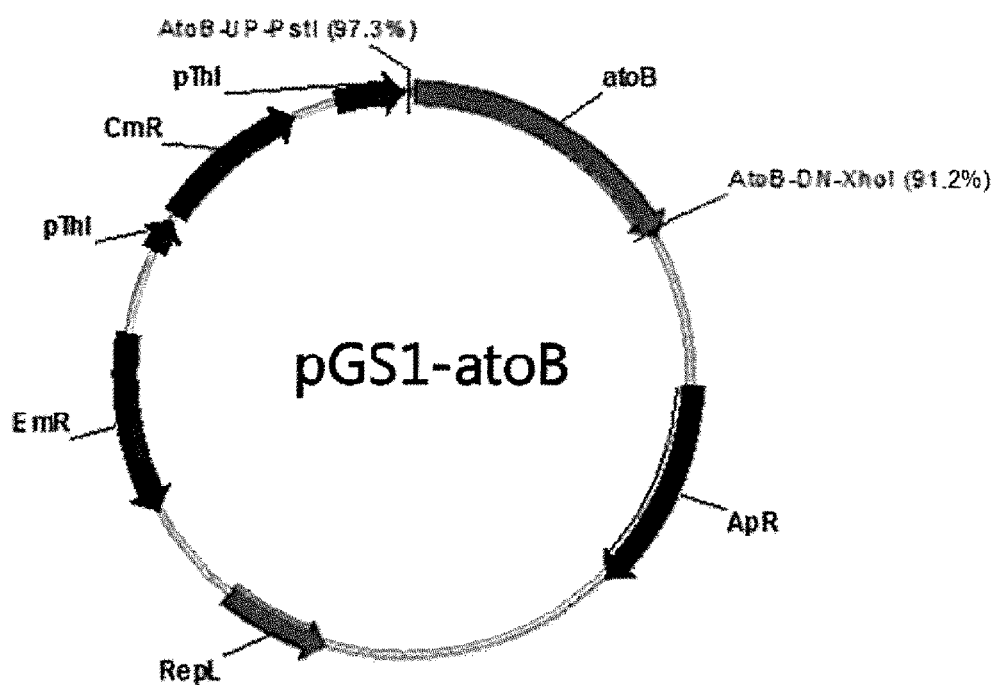
FIG. 4 shows a pGS1-atoB vector.

The amplified gene was purified on 1% agarose gel, and then digested with PstI and XhoI restriction enzymes to cleave a DNA fragment. pGS1-MCS vector (FIG. 3) was digested with the same restriction enzymes, and the DNA fragment was ligated to construct pGS1-atoB (FIG. 4).

TABLE 1

| SEQ ID NO 1 | atgaaaaattgtgtcatcgtcagtgcggtacgtactgct<br>atcggtagttttaacggttcactcgcttccaccagcgcc<br>atcgacctgggggcgacagtaattaaagccgccattgaa<br>cgtgcaaaaatcgattcacaacacgttgatgaagtgatt<br>atgggtaacgtgttacaagccgggctggggcaaaatccg<br>gcgcgtcaggcactgttaaaaagcgggctggcagaaacg<br>gtgtgcggattcacggtcaataaagtatgtggttcgggt<br>cttaaaagtgtggcgcttgccgcccaggccattcaggca<br>ggtcaggcgcagagcattgtggcgggggtatggaaaat<br>atgagtttagcccctacttactcgatgcaaaagcacgc<br>tctggttatcgtcttggagacggacaggtttatgacgta<br>atcctgcgcgatggcctgatgtgcgccacccatggttat<br>catatggggattaccgccgaaaacgtggctaaagagtac<br>ggaattaccgtgaaatgcaggatgaactggcgctacat<br>tcacagcgtaaagcggcagccgcaattgagtccggtgct<br>tttacagccgaaatcgtcccggtaaatgttgtcactcga<br>aagaaaaccttcgtcttcagtcaagacgaattcccgaaa<br>gcgaattcaacggctgaagcgttaggtgcattgcgcccg<br>gccttcgataaagcaggaacagtcaccgctgggaacgcg<br>tctggtattaacgacggtgctgccgctctggtgattatg<br>gaagaatctgcggcgctggcagcaggcctaccccctg<br>gctcgcattaaaagttatgccagcggtggcgtgcccccc<br>gcattgatgggtatggggccagtacctgccacgcaaaaa<br>gcgttacaactggcggggctgcaactggcggatattgat<br>ctcattgaggctaatgaagcatttgctgcacagttcctt<br>gccgttgggaaaaacctgggctttgattctgagaaagtg<br>aatgtcaacggcggggccatcgcgctcgggcatcctatc<br>ggtgccagtggtgctcgtattctggtcacactattacat<br>gccatgcaggcacgcgataaaacgctggggctggcaaca<br>ctgtgcattggcggcggtcagggaattgcgatggtgatt<br>gaacggttgaattaa |
| --- | --- |
| SEQ ID NO 2 | atoB-UP-PstI: 5'-ATACTGCAGATGAAAAATTG TGTCATCGTCAGTGCGG-3' |
| SEQ ID NO 3 | atoB-DN-XhoI: 5'-ATACTCGAGTTAATTCAACC GTTCAATCACCATC-3' |

Construction of pGS1-HCB

First of all, *Clostridium acetobutylicum* ATCC 824 was streaked on solid RCM medium, followed by anaerobic culturing for 48 hours. A colony selected from the streaked solid medium was cultured in 3 ml of a liquid RCM culture medium for 18 hours, followed by centrifuging the culture solution to obtain cells. The cells were washed with 10 ml Tris buffer, followed by purification using a Wizard Genomic DNA Purification Kit (manufactured by Promega Corp., USA) to isolate chromosome of the strain.

hbd-crt-bcd operon (SEQ ID NO: 4, FIG. 5) of *Clostridium acetobutylicum* ATCC 824 was amplified using primers HCB-UP-PstI (SEQ ID NO: 5) and HCB-DN-XhoI (SEQ ID NO: 6) (Table 2).

100 µl of PCR mixture includes 250 µM dNTP, 20 pmol of each primer, 1.5 mM $MgCl_2$, 10 µl of 10× buffer, 100 ng of DNA template, and 5 units of pfu polymerase. In PCR, the reaction was repeated for 30 cycles consisting of initial denaturing at 95° C. for 5 minutes, followed by denaturing at 95° C. for 1 minute, annealing at 50° C. for 1 minute and then polymerizing at 72° C. for 4 minutes.

Figure 6:
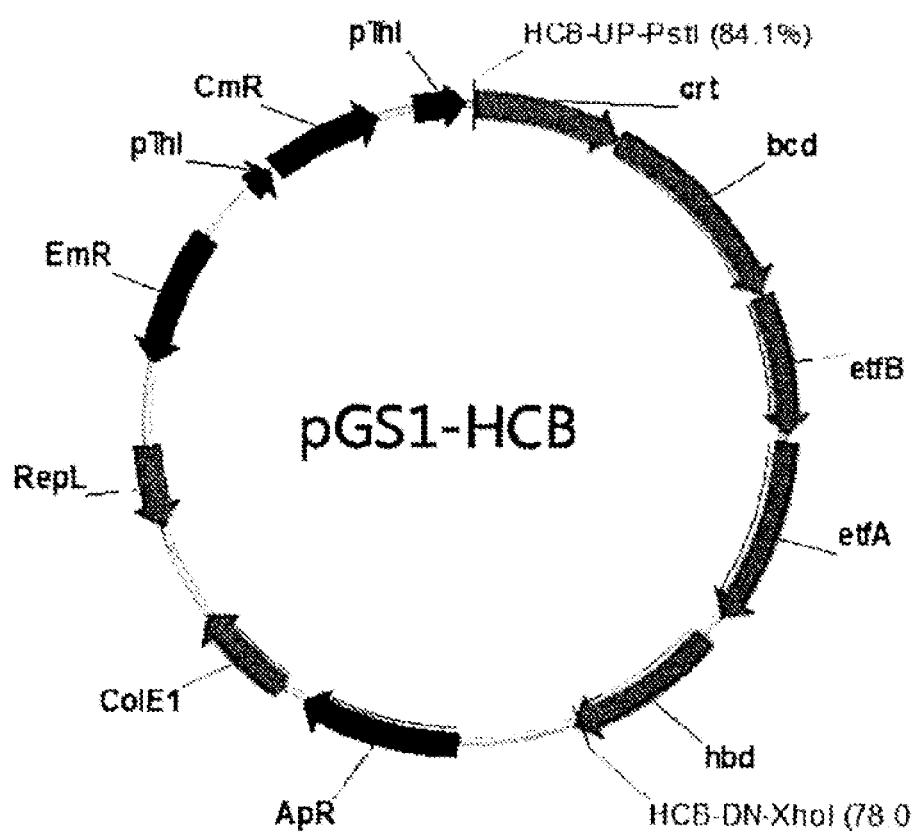
FIG. 6 shows a pGS1-HCB vector.

The amplified gene was purified on 1% agarose gel, and digested with PstI and XhoI restriction enzymes to cleave the DNA fragment, which was then ligated to a pGS1-MCS vector to construct pGS1-HCB (FIG. 6).

TABLE 2

| SEQ ID NO 5 | HCB-UP-PstI:<br>5'-ATACTGCAGATGGAACTAAACAAT GTCATCCTTGAAAAGGAAGG-3' |
| --- | --- |
| SEQ ID NO 6 | HCB-DN-XhoI:<br>5'-ATACTCGAGTTATTTTGAATAATC GTAGAAACCTTTTCCTG-3' |

Construction of pGS1-E1AB

Figure 7:
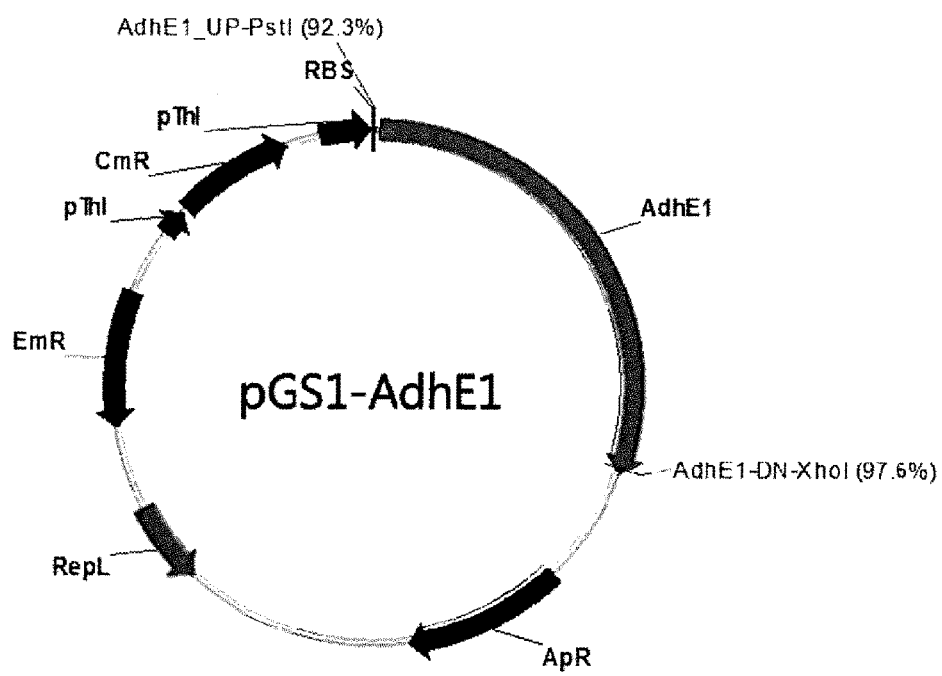
FIG. 7 shows a pGS1-AdhE1 vector.

*Clostridium acetobutylicum* ATCC 824 was streaked on solid RCM medium, followed by anaerobic culturing for 24 hours. A colony selected from the streaked solid medium was cultured in 3 ml of a liquid culture medium for 18 hours, followed by centrifuging the culture solution to obtain cells. The cells were washed with 10 ml Tris buffer, followed by purification using a Wizard Genomic DNA purification Kit (manufactured by Promega Corp., USA) to isolate chromosome of the strain.

adhE1 gene (SEQ ID NO: 7) was amplified using primers AdhE1-UP-PstI (SEQ ID NO: 8) and AdhE1-DN-XhoI (SEQ ID NO: 9) and using the isolated chromosome as a template (Table 3). 100 µl of PCR mixture includes 250 µM dNTP, 20 pmol of each primer, 1.5 mM $MgCl_2$, 10 µl of 10× buffer, 100 ng of DNA template, and 1 unit of pfu polymerase. In PCR, the reaction was repeated for 30 cycles consisting of initial denaturing at 95° C. for 5 minutes, followed by denaturing at 95° C. for 1 minute, annealing at 50° C. for 1 minute and then polymerizing at 72° C. for 2 minute. The amplified gene was purified on 1% agarose gel, and then digested with PstI and XhoI restriction enzymes to cleave the DNA fragment. pGS1-MCS vector was digested with the same restriction enzymes, and the DNA fragment was ligated to construct pGS1-AdhE1 (FIG. 7).

TABLE 3

| SEQ ID NO 7 | atgaaagtcacaacagtaaaggaattagatgaaaaactcaa<br>ggtaattaaagaagctcaaaaaaaattctcttgttactcgcaag<br>aaatggttgatgaaatcttttagaaatgcagcaatggcagcaatcga<br>cgcaaggatagagctagcaaaagcagctgttttggaaaccggtatg<br>ggcttagttgaagacaaggttataaaaaatcattttgcaggcgaat<br>acatctataacaaatataaggatgaaaaaacctgcggtataattga<br>acgaaatgaaccctacggaattacaaaaaatagcagaacctatagga<br>gttgtagctgctataatccctgtaacaaacccacatcaacaacaa<br>tatttaaatccttaatatcccttaaaactagaaatggaattttctt<br>ttcgcctcacccaagggcaaaaaaatccacaatactagcagctaaa<br>acaatacttgatgcagccgttaagagtggtgccccggaaaatataa<br>taggttggatagatgaaccttcaattgaactaactcaatatttaat<br>gcaaaaagcagatataaccccttgcaactggtggtccctcactagtt<br>aaatctgcttattcttccggaaaaccagcaataggtgttggtccgg |
| --- | --- |

TABLE 3-continued

```
gtaacaccccagtaataattgatgaatctgctcatataaaaatggc
agtaagttcaattatattatccaaaacctatgataatggtgttata
tgtgcttctgaacaatctgtaatagtcttaaaatccatatataaca
aggtaaaagatgagttccaagaaagaggagcttatataataaagaa
aaacgaattggataaagtccgtgaagtgattttttaaagatggatcc
gtaaaccctaaaatagtcggacagtcagcttatactatagcagcta
tggctggcataaaagtacctaaaaccacaagaatattaataggaga
agttacctccttaggtgaagaagaacctttgcccacgaaaaacta
tctcctgttttggctatgtatgaggctgacaattttgatgatgctt
taaaaaaagcagtaactctaataaacttaggaggcctcggccata
cctcaggaatatatgcagatgaaataaaagcacgagataaatagat
agatttagtagtgccatgaaaaccgtaagaaccttgtaaatatcc
caacctcaccaaggtgcaagtggagatctatataattttagaatac
caccttcttcacgcttggctgcggattttgggaggaaattctgt
ttccgagaatgttggtccaaaacatcttttgaatattaaaaccgta
gctgaaaggagagaaaacatgctttggtttagagttccacataaag
tatattttaagttcggttgtcttcaatttgctttaaaagatttaaa
agatctaaaagaaaaaaagagcctttatagttactgatagtgaccc
ctataatttaaactatgttgattcaataataaaaatacttgagcac
ctagatattgattttaaagtatttaataaggttggaagagaagctg
atcttaaaaccataaaaaagcaactgaagaaatgtcctccttat
gccagacactataatagctttaggtggtaccctgaaatgagctcg
caaagctaatgtgggtactatatgaacatccagaagtaaaatttga
agatcttgcaataaaatttatggacataagaaagagaatatatctt
tcccaaactcggtaaaaaggctatgttagttgcaattacaacttct
gctggttccggttctgaggttactccttttgctttagtaactgaca
ataacactggaaataagtacatgttagcagattatgaaatgacacc
aaatatggcaattgtagatgcagaacttatgatgaaaatgccaaag
ggattaaccgcttattcaggtatagatgcactagtaaatagtatag
aagcatacacatccgtatgcttcagaatacacaaacggactagc
actagaggcaatacgattaatatttaaatatttgcctgaggcttac
aaaaacggaagaaccaatgaaaagcaagagagaaaatggctcacgc
ttcaactatggcaggtatggcatccgctaatgcatttctaggtcta
tgtcattccatggcaataaaattaagttcagaacacaatattccta
gtggcattgccaatgccaatgcattactaatagaagaagtaataaa
atttaacgcagttgataatcctgtaaaacaagcccttgcccacaa
tataagtatccaaacaccatatttagatatgctcgaattgcagatt
atataaagcttggaggaaatactgatgaggaaaaggtagatctctt
aattaacaaaatacatgaactaaaaaaagcttaaatataccaactt
caataaaggatgcaggtgttttggaggaaaacttctattcctccct
tgatagaatatctgaacttgcactagatgatcaatgcacaggcgct
aatcctagatttcctcttacaagtgagataaaagaaatgtatataa
attgttttaaaaaacaaccttaa
```

SEQ ID NO 8  AdhE1-UP-PstI: 5'-CACCTGCAGATGAAAGTCACA ACAGTAAAGGAATTAGAT-3'

SEQ ID NO 9  AdhE1-DN-XhoI: 5'-CACCTCGAGTTAAGGTTGTTT TTTAAAACAATTTATATACA-3' pGS1-E1AB was constructed using previously constructed recombinant plasmids. First of all, ctfAB gene (SEQ ID NO: 10) was amplified using primers CtfAB-UP-XhoI (SEQ ID NO: 11) and E1AB-DN-SalI (SEQ ID NO: 12) and using the isolated chromosome of *Clostridium acetobutylicum* ATCC 824 as a template (Table 4).

Figure 8:
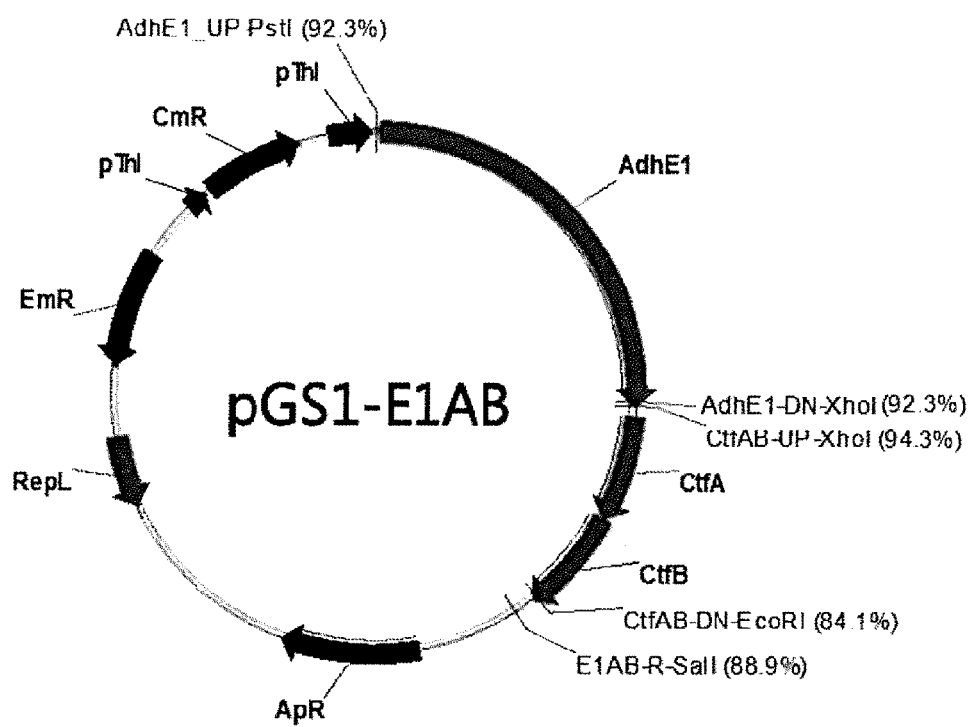
FIG. 8 shows a pGS1-E1AB vector.

The amplified gene was purified on a 1% agarose gel, and digested with XhoI and SalI restriction enzymes to cleave the DNA fragment. A pGS1-AdhE1 vector was digested with the same restriction enzymes, and the DNA fragment was ligated to construct pGS1-E1AB (FIG. 8).

TABLE 4

```
SEQ ID NO 10
accttcatatttcaactacttttttataattttaataaaga
atttaaaaggagggattaaaatgaactctaaaataattag
atttgaaaatttaaggtcattctttaaagatgggatgacaattgatga
ttggaggtttttttaaactgtggcactccaaccaaattaattgatttt
ttagttaatttaaatataaagaatttaacgattataagtaatgatac
atgttatcctaatacaggtattggtaagttaatatcaaataatcaag
taaaaaagcttattgcttcatatataggcagcaacccagatactggc
aaaaaacttttttaataatgaacttgaagtagagctctctcccccaagg
aactctagtggaaagaatacgtgcaggcggatctggcttaggtggtg
ggaactttgattgaaaaaggaaagaaaaaatatctatataatggaacg
gaatatttgttagagctacctcttacagccgatgtagcattaattaa
aggtagtattgtagatgaggccggaaacaccttctataaaggtacta
ctaaaaactttaatccctatatggcaatggcagctaaaaccgtaata
gttgaagctgaaatttagttagctgtgaaaaactagaaaaggaaaaa
gcaatgaccccggagttcttataaattatatagtaaaggagcctgc
ataaaatgattaatgataaaaacctagcgaaagaaataatagccaaa
agagttgcaagagaattaaaaaatggtcaacttgtaaacttaggtgt
aggtcttcctaccatggttgcagattatataccaaaaaatttcaaaa
ttactttccaatcagaaaacggaatagttggaatgggcgctagtcct
aaaataaatgaggcagataaagatgtagtaaatgcaggaggagacta
tacaacagtacttcctgacggcacattttctcgatagctcagtttcgt
tttcactaatccgtggtggtcacgtagatgttactgttttagggggct
ctccaggtagatgaaaagggtaatatagccaattggattgttcctgg
aaaaatgctctctggtatgggtggagctatggatttagtaaatggag
ctaagaaagtaataatgcaatgagacatacaaataaaggtcaaccta
aaattttaaaaaaatgtacacttcccctcacggcaaagtctcaagca
aatctaattgtaacagaacttggagtaattgaggttattaatgatgg
tttacttctcactgaaattaataaaaacacaaccattgatgaaataa
ggtcttttaactgctgcagatttactcatatccaatgaacttagaccc
atggctgtttagaaagaaatactatgaaacaatattaaaaaaataag
agttaccatttaaggtaactcttattttttattacttaagataatcat
atataacttcagctctaggcaatattatatctgcaagaatgtgagag
ctagaaacaatctcttttactggc
```

SEQ ID NO 11  CtfAB-UP-XhoI: 5'-CACCTCGAGACCTTCATATTTC AACTACTTTTTAT-3'

SEQ ID NO 12  E1AB-DN-SalI: 5'-TACGCGTCGACGCCAGTAAAAGA GATTGTTTCTAGC-3'

Construction of pGS1-E1 AB-atoB pGS1-E1AB-atoB was constructed using previously constructed recombinant plasmids pGS1-atoB and pGS1-E1AB.

First, atoB gene (SEQ ID NO: 1) and promoter and terminator regions of the plasmid were amplified using primers pTh1-UP-SalI (SEQ ID NO: 13) and pGS-R4 (SEQ ID NO: 14) and using the constructed pGS1-atoB as a template (Table 5). 100 μl of PCR mixture includes 250 μM dNTP, 20 pmol of each primer, 1.5 mM MgCl$_2$, 10 μl of 10× buffer, 100 ng of DNA template, and 1 unit of pfu polymerase. In PCR, the reaction repeated 25 cycles consisting of initial denaturing at 95° C. for 5 minutes, followed by denaturing at 95° C. for 1 minute, annealing at 50° C. for 1 minute and then polymerizing at 72° C. for 4 minute.

Figure 9:
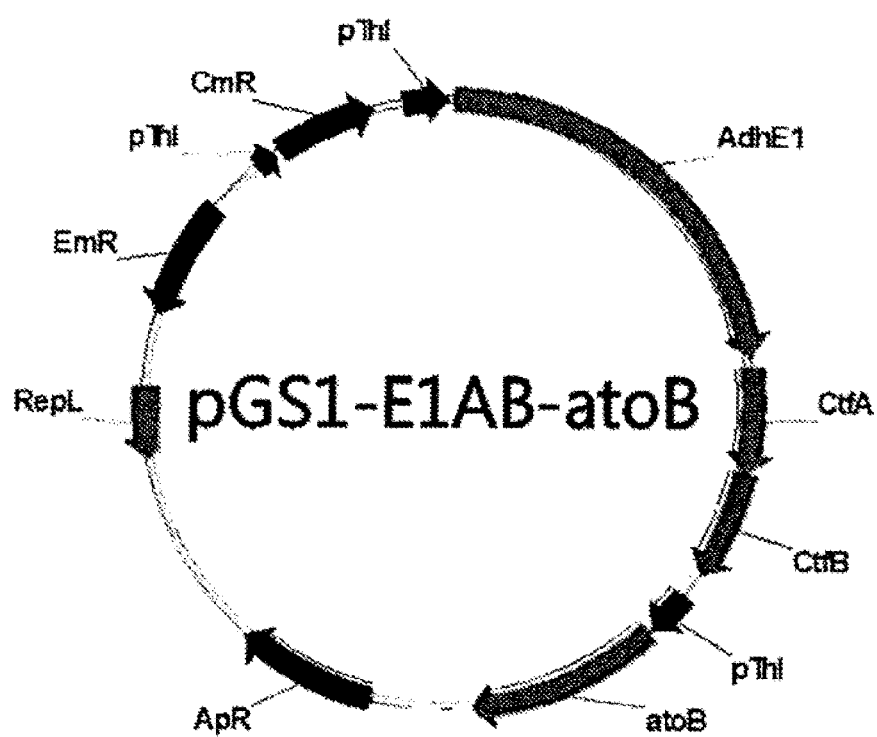
FIG. 9 shows a pGS1-E1AB-atoB vector.

The amplified gene was purified on a 1% agarose gel, and then digested with SalI and XmaI restriction enzymes to cleave a DNA fragment. pGS1-E1AB vector was digested with the same restriction enzymes, and the DNA fragment was ligated to construct pGS1-E1AB-atoB (FIG. 9).

TABLE 5

| SEQ ID NO 13 | pTh1-UP-SalI: 5'-ATAGTCGACATGAAGTTT CTTATGCACAAGTATTTTTTATTACATTAA-3' |
|---|---|
| SEQ ID NO 14 | pGS-R4. 5'-TAAGTTGGGTAACGCCAGGG-3' |

Construction of pGS1-E1AB-HCB pGS1-E1AB-HCB was constructed using the previously constructed recombinant plasmids pGS1-HCB and pGS1-E1AB.

A gene encoding hbd-crt-bcd operon (SEQ ID NO: 4) and promoter and terminator regions were amplified using primers pTh1-UP-SalI (SEQ ID NO: 13) and pGS-R4 (SEQ ID NO: 14) and using pGS1-HCB constructed in the above as a template. 100 μl of PCR mixture includes 250 μM dNTP, 20 pmol of each primer, 1.5 mM MgCl$_2$, 10 μl of 10× buffer, 100 ng of DNA template, and 5 units of pfu polymerase. In PCR, the reaction was repeated for 30 cycles consisting of initial denaturing at 95° C. for 5 minutes, followed by denaturing at 95° C. for 1 minute, annealing at 50° C. for 1 minute and then polymerizing at 72° C. for 1 minute.

Figure 10:
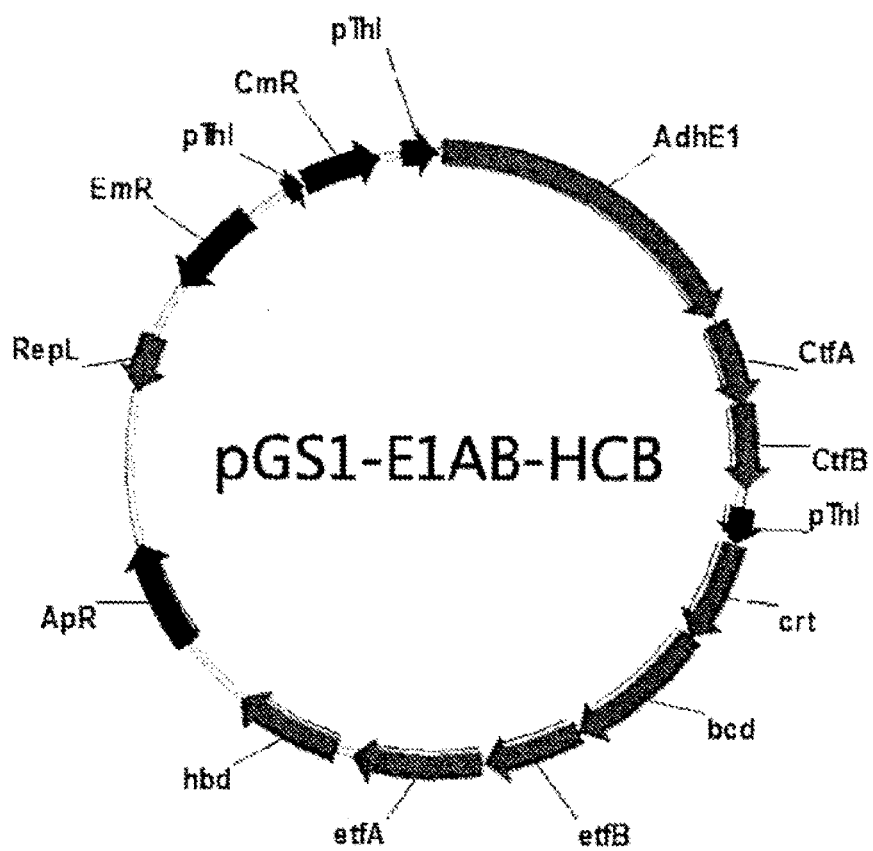
FIG. 10 shows a pGS1-E1AB-HCB vector.

The amplified gene was purified on a 1% agarose gel, and then digested with SalI and XmaI restriction enzymes to cleave a DNA fragment. pGS1-E1AB vector was digested with the same restriction enzymes, the DNA fragment was ligated to construct pGS1-E1AB-HCB (FIG. 10).

<Experimental Example 2> Construction of Recombinant Microorganism

The recombinant plasmids manufactured in the Experimental Example 1 were introduced into the gene deleted strains listed in Table 6 to construct recombinant microorganisms.

TABLE 6

| gene deleted strain |
| --- |
| *Clostridium acetobutylicum* PJC4BK Δbuk::MLS$^r$ |
| *Clostridium acetobutylicum* ATCC824 Δpta |
| *Clostridium acetobutylicum* ATCC824 Δpta Δbuk |

Each gene deleted *Clostridium* strain was cultured in 60 ml of liquid CGM (*Clostridium* Growth Media) (0.75 g/L K$_2$HPO$_4$, 0.75 g/L KH$_2$PO$_4$, 0.7 g/L, MgSO$_4$.7H$_2$O, 0.017 g/L MnSO$_4$.5H$_2$O, 0.01 g/L, FeSO$_4$.7H$_2$O, 2 g/L (NH$_4$)$_2$SO$_4$, 1 g/L NaCl, 2 g/L asparagine, 0.004 g/L p-aminobenzoic acid, 5 g/L, yeast extract, 4.08 g/L CH$_3$COONa.3H$_2$O, and 80 g/L glucose) under anaerobic conditions until OD600 became 0.5. The culture solution was stood on ice for 10 minutes, followed by centrifuging the culture solution at 7000 g at 4° C. for 10 minutes. The cell pellets were washed with an electroporation buffer solution three times, and suspended in 2 ml of the same buffer solution to manufacture cells for transformation. To 500 μl of the prepared cells for transformation, 0.5~2.0 μg of plasmids were added to perform electroporation (4 mm cuvette, 2.5 kV, ∞Ω, 25 uF) by Gene Pulser II manufactured by Bio-Rad Corporation. Subsequently, the cells were cultured anaerobically in a medium with antibiotics to obtain transformed strains (Table 7).

The plasmids used for transformation were all methylated in *E. coli* TOP10 strain transformed with a pAN1 vector prior to electroporation such that the plasmids could not be affected by restriction system of *Clostridium* strains.

TABLE 7

| # | strain | introduced plasmid |
| --- | --- | --- |
| 1 | *Clostridium acetobutylicum* PJC4BK Δbuk::MLS$^r$ | — |
| 2 | *Clostridium acetobutylicum* PJC4BK Δbuk::MLS$^r$ | pGS1-HBC |
| 3 | *Clostridium acetobutylicum* PJC4BK Δbuk::MLS$^r$ | pGS1-atoB |
| 4 | *Clostridium acetobutylicum* PJC4BK Δbuk::MLS$^r$ | pGS1-E1AB |
| 5 | *Clostridium acetobutylicum* PJC4BK Δbuk::MLS$^r$ | pGS1-E1AB-HCB |
| 6 | *Clostridium acetobutylicum* PJC4BK Δbuk::MLS$^r$ | pGS1-E1AB-atoB |
| 7 | *Clostridium acetobutylicum* ATCC824 Δpta | — |
| 8 | *Clostridium acetobutylicum* ATCC824 Δpta | pGS1-HBC |
| 9 | *Clostridium acetobutylicum* ATCC824 Δpta | pGS1-atoB |
| 10 | *Clostridium acetobutylicum* ATCC824 Δpta | pGS1-E1AB |
| 11 | *Clostridium acetobutylicum* ATCC824 Δpta | pGS1-E1AB-HCB |
| 12 | *Clostridium acetobutylicum* ATCC824 Δpta | pGS1-E1AB-atoB |
| 13 | *Clostridium acetobutylicum* ATCC824 Δpta Δbuk | — |
| 14 | *Clostridium acetobutylicum* ATCC824 Δpta Δbuk | pGS1-HBC |
| 15 | *Clostridium acetobutylicum* ATCC824 Δbuk Δbuk | pGS1-atoB |
| 16 | *Clostridium acetobutylicum* ATCC824 Δpta Δbuk | pGS1-E1AB |
| 17 | *Clostridium acetobutylicum* ATCC824 Δpta Δbuk | pGS1-E1AB-HCB |
| 18 | *Clostridium acetobutylicum* ATCC824 Δpta Δbuk | pGS1-E1AB-atoB |

MLS$^r$, macrolide lincosamide streptogramin B resistance

<Experimental Example 3> Production of Biobutanol by Batch Culture

Throughout batch culture, butanol production ability depending on the recombinant microorganisms was tested. The recombinant *Clostridium* strains (#1 to #18) constructed in Experimental Example 2 were streaked on a solid CGM medium, followed by anaerobic culture at 37° C. overnight. Each of the cultured colony was inoculated to a 50 ml disposable tube (manufactured by Falcon, USA) containing 40 ml of CCM, followed by standing at 37° C., and then cultured anaerobically until OD600 became 1. The cultured microorganisms were inoculated again to a liquid CGM medium containing 400 ml of 6% glucose, followed by standing at 37° C., and then culturing anaerobically until OD600 became 1. The resulting microorganisms were inoculated to a fermenter including 1.6 L of liquid CGM medium to which 8% glucose was added, thereby initiating cultivation. pH was maintained at pH 5.0 using ammonium hydroxide (NH$_4$OH) during the anaerobic culture, wherein the anaerobic conditions were maintained by purging nitrogen at a speed of 20 ml/min. The concentration of the produced butanol and mixed solvent was analyzed every three hours after the cultivation. The analysis of butanol and mixed solvent was performed using a gas chromatography (Agilent, USA). The analysis conditions are summarized in Table 8. The culture solution was centrifuged to give a supernatant, which was then subjected to HPLC and sugar analyzer to determine the concentration of sugars and organic acids. In HPLC, water containing 0.01N sulfuric acid was used as a mobile phase, and flow rate was 0.6 ml/min. As columns, Aminex87H and Aminex87P (Bio-Rad, USA) were employed. The sugars and organic acids were analyzed using an RI (Reflective Index) detector. As a control group, wild type *C. acetobutylicum* ATCC 824 was used (C1).

TABLE 8

| | |
| --- | --- |
| Injector temperature | 320° C. |
| Detector temperature | 320° C. |
| Injector Split ratio | 20/1 |

TABLE 8-continued

| | |
|---|---|
| Injection volume | 0.1 ul |
| Oven condition | 80° C./15 min |
| Air flow | 300 mL/min |
| H2 flow | 30 mL/min |
| column | Supelco CarboWAX |

Comparing #1~#3 strains, it was confirmed that ethanol selectivity was greatly reduced from 17% to 7% when HCB operon and atoB gene were overexpressed in buk gene-deleted PJC4BK strain. Since ethanol causes toxicity to microorganisms, it is very important to keep the concentration of ethanol low when butanol is produced through continuous fermentation. However, in the case of #2 and #3 strains, although ethanol selectivity is decreased, there are problems that butanol productivity and yield are still low.

On the other hand, comparing strain #1 with strain #4, it was confirmed that butanol productivity was enhanced when adhE1 and ctfAB were overexpressed simultaneously in PJC4BK strain. Accordingly, the present inventors aimed to increase butanol productivity and keep ethanol selectivity low by overexpressing atoB gene or HCB operon in #4 strain. As a result, comparing strains #2 and #3 with strains #5 and #6, respectively, it was confirmed that butanol productivity was increased by 41% and 17%, respectively.

However, in the case of #5 and #6 strains, it was confirmed that ethanol selectivity was slightly increased from 7% to 16% and 13%, respectively.

On the contrary, pta gene-deleted strains (#7~#12) exhibited generally low yield and specifically low ethanol selectivity. From the result, it was determined that the deletion of pta gene decreased ethanol selectivity. In this regard, the present inventors estimated that a further deletion of pta in strains #5 and #6 would reduce ethanol selectivity while keeping butanol productivity high. Based on such estimation, the performances of strains #17 and #18 were measured. In the case of strain #17, it was confirmed that ethanol selectivity was decreased by half, and butanol productivity, selectivity and ABE yield were improved by 7%, 21% and 15%, respectively, as compared to strain #5. On the other hand, in the case of strain #18, it was confirmed that ethanol selectivity was decreased by 7%, butanol selectivity was also decreased by about 4%, and butanol productivity and yield were increased by 11%, 10%, respectively, as compared to strain #6.

In summary, it could be confirmed that butanol productivity and yield tended to increase, when adhE and ctfAB were simultaneously overexpressed in a strain in which pta and buk related to organic acid production were deleted. In addition, it could be confirmed that, when atoB or HCB operon were further overexpressed, ethanol selectivity was decreased while butanol selectivity was increased (Table 9).

TABLE 9

| # | strain | introduced plasmid | acetone (g/L) | ethanol (g/L) | butanol (g/L) | total ABE (g/L) | ethanol selectivity (%) | butanol selectivity (%) | butanol productivity (g/L/h)* | yield (%) |
|---|---|---|---|---|---|---|---|---|---|---|
| Cl. | C. acetobutylicum ATCC824 | — | 4.413 | 0.981 | 12.784 | 18.18 | 5.4 | 70.3 | 0.489 | 22 |
| 1 | Clostridium acetobutylicum PJC4BK Δbuk::MLS* | — | 4.478 | 4.114 | 16.040 | 24.632 | 17 | 65.0 | 1.03 | 30 |
| 2 | Clostridium acetobutylicum PJC4BK Δbuk::MLS | pGS1-HBC | 5.043 | 1.391 | 13.536 | 19.970 | 7 | 67.8 | 0.792 | 29 |
| 3 | Clostridium acetobutylicum PJC4BK Δbuk::MLS | pGS1-atoB | 2.168 | 1.317 | 15.929 | 19.414 | 7 | 82.0 | 0.992 | 28 |
| 4 | Clostridium acetobutylicum PJC4BK Δbuk::MLS | pGS1-E1AB | 4.222 | 3.199 | 14.553 | 21.974 | 15 | 66.2 | 1.728 | 30 |
| 5 | Clostridium acetobutylicum PJC4BK Δbuk::MLS | pGS1-E1AB-HCB | 3.633 | 3.254 | 14.337 | 21.224 | 16 | 67.6 | 1.060 | 28 |
| 6 | Clostridium acetobutylicum PJC4BK Δbuk::MLS | pGS1-E1AB-atoB | 1.249 | 2.575 | 16.832 | 20.656 | 13 | 81.5 | 1.155 | 32 |
| 7 | Clostridium acetobutylicum ATCC824 Δpta | — | 3.521 | 1.519 | 12.160 | 17.20 | 9 | 70.2 | 1.114 | 24 |
| 8 | Clostridium acetobutylicum ATCC824 Δpta | pGS1-HBC | 1.417 | 0.948 | 9.457 | 11.822 | 8 | 80.0 | 0.772 | 25 |
| 9 | Clostridium acetobutylicum ATCC824 Δpta | pGS1-atoB | 2.632 | 0.979 | 9.062 | 12.693 | 8 | 71.6 | 0.626 | 22 |
| 10 | Clostridium acetobutylicum ATCC824 Δpta | pGS1-E1AB | 5.452 | 1.951 | 16.317 | 23.720 | 8 | 68.8 | 1.341 | 30 |
| 11 | Clostridium acetobutylicum ATCC824 Δpta | pGS1-E1AB-HCB | 4.743 | 2.325 | 15.617 | 22.685 | 10 | 68.8 | 1.102 | 28 |
| 12 | Clostridium acetobutylicum ATCC824 Δpta | pGS1-E1AB-atoB | 4.839 | 2.752 | 15.980 | 23.571 | 12 | 67.8 | 1.179 | 27 |
| 13 | Clostridium acetobutylicum ATCC824 Δpta Δbuk | — | 3.678 | 2.456 | 16.393 | 22.539 | 11 | 72.7 | 0.938 | 29 |
| 14 | Clostridium acetobutylicum ATCC824 Δpta Δbuk | pGS1-HBC | 3.475 | 4.134 | 14.057 | 21.655 | 19 | 64.9 | 1.027 | 30 |
| 15 | Clostridium acetobutylicum ATCC824 Δpta Δbuk | pGS1-atoB | 2.445 | 1.771 | 15.535 | 19.751 | 9 | 78.7 | 0.982 | 32 |
| 16 | Clostridium acetobutylicum ATCC824 Δpta Δbuk | pGS1-E1AB | 1.315 | 2.386 | 14.813 | 18.514 | 13 | 80.0 | 1.310 | 32 |
| 17 | Clostridium acetobutylicum ATCC824 Δpta Δbuk | pGS1-E1AB-HCB | 2.115 | 1.666 | 17.029 | 20.816 | 8 | 61.8 | 1.133 | 32 |
| 18 | Clostridium acetobutylicum ATCC824 Δpta Δbuk | pGS1-E1AB-atoB | 2.058 | 2.427 | 16.356 | 20.841 | 12 | 78.5 | 1.282 | 35 |

*Productivity is based on exponential phase.

<Experimental Example 4> Production of Biobutanol Using Fed-Batch Culture Method

6, #16~#18 recombinant strains which were determined to have excellent butanol selectivity, butanol productivity and yield, and low ethanol selectivity in Experimental Example 3 were subjected to fed-batch cultivation in a culture medium containing an adsorbent capable of selectively adsorbing butanol.

First, recombinant *Clostridium* strains #6, #16, #17 and #18 constructed in Experimental Example 2 were streaked on solid CGM, followed by culturing anaerobically at 37° C. overnight. Each of the cultured colony was inoculated to a 50 ml disposable tube (manufactured by Falcon, USA) containing 40 ml of CCM, followed by standing at 37° C., and culturing the colony anaerobically until OD600 became 1. The cultured microorganism was again inoculated to liquid CGM containing 400 ml of 6% glucose, followed by standing at 37° C., and culturing the colony anaerobically until OD600 became 1. The obtained microorganism was inoculated to a fermenter containing 1.6 L of liquid CGM containing 8% glucose and 200 g of an adsorbent capable of selectively adsorbing butanol, and then cultured. pH was maintained at pH 5.0 using ammonium hydroxide (NH$_4$OH) during anaerobic cultivation, wherein the anaerobic conditions were maintained by purging nitrogen at a speed of 20 ml/min. The concentration of the produced butanol and mixed solvent was analyzed every three hours after the cultivation. In order to maintain the glucose concentration in the culture solution at 10 g/L or more, 700 g/L glucose solution was used as a feeding solution.

In order to produce butanol through continuous cultivation with high yield, high productivity and high selectivity, it is very important to keep the concentration of ethanol low such that ethanol does not cause toxicity to strains during the culture period. As can be seen from results of fed-batch cultivation, it was confirmed that strains #17 and #18 maintained very low ethanol selectivity while maintaining high performance as butanol producing strains. Accordingly, these strains were expected to be suitable for long-term continuous culture (Table 10).

adsorbent. Two columns were prepared. These incubators were linked by a silicon tube, followed by providing pumps, thereby allowing a culture solution to be circulated between the columns. As the inlet and outlet for the columns, 4-way valves were provided such that, in the course of culturing, the columns could be subjected to desorption in real time by flowing a solvent for elution when the adsorbent in the columns was saturated with butanol and mixed solvent. In the case that the first column was subjected to desorption, the culture solution was circulated to the second column such that the culture solution flew continuously. The culture solution was circulated in a direction from upper to lower of the column, but the direction is not particularly limited. #16 strain (control group), #17 and #18 strains having butanol and mixed solvent productivity were cultured in the incubator manufactured above. First, 800 ml of microorganism which was anaerobically cultured in liquid CGM overnight was inoculated to an incubator comprising 3.2 L liquid CGM to initiate culture. In the present Experimental Example, the microorganism was cultured by general batch fermentation. After initiation of the culture, the culture solution was circulated by passing through columns with a flow rate of 50 ml/min through a pump when the butanol concentration became about 7 g/L~8 g/L. As the culture solution passed through the columns, the adsorbent was suspended in the culture solution to form a slurry phase, which prevented the culture solution from flocking, thereby passing through the columns. The butanol concentration was maintained at 8 g/L or less just before and after the culture solution passed through the columns.

As a result, it could be confirmed that yield, selectivity and productivity were all excellent, particularly remarkable enhancement was found in view of process stability (culture period) when hcb operon or atoB encoding thiolase were overexpressed. However, in the case of recombinant strain #16 in which HCB operon or thiolase was not overexpressed, as the culture period got longer, ethanol was accumulated in high concentration, which greatly deteriorated performance of the strain, particularly in view of butanol and mixed solvent productivity. Accordingly, it was impossible to culture the microorganism for more than 88 hours.

TABLE 10

| # | strain | introduced plasmid | acetone (g/L) | ethanol (g/L) | butanol (g/L) | total ABE (g/L) | ethanol selectivity (%) | butanol selectivity (%) | butanol productivity (g/L/h)* | yield (%) |
|---|---|---|---|---|---|---|---|---|---|---|
| 6 | *Clostridium acetobutylicum* PJC4BK Δbuk::MLS | pGS1-E1AB-atoB | 1.719 | 4.636 | 24.278 | 30.633 | 16 | 79.3 | 1.003 | 32 |
| 16 | *Clostridium acetobutylicum* ATCC824 Δpta Δbuk | pGS1-E1AB | 2.043 | 6.156 | 26.592 | 34.892 | 18 | 76.5 | 1.550 | 35 |
| 17 | *Clostridium acetobutylicum* ATCC824 Δpta Δbuk | pGS1-E1AB-HCB | 2.439 | 2.540 | 23.886 | 28.865 | 9 | 82.8 | 1.106 | 33 |
| 18 | *Clostridium acetobutylicum* ATCC824 Δpta Δbuk | pGS1-E1AB-atoB | 3.856 | 2.646 | 26.403 | 32.908 | 8 | 80.2 | 1.103 | 33 |

<Experimental Example 5> Production of Biobutanol Using Continuous Culture Method Based on the results from Experimental Example 4, recombinant strains #16, #17 and #18 were tested for the performance of butanol producing strains through continuous cultivation. First, an incubator for continuous culture process was manufactured in accordance with Korean patent application no. 10-2012-0038770. At upper and lower ends of a 3 L column, a filter having a size of about 150 μm was provided in order to prevent an adsorbent from elution, followed by providing a stirrer and charging 200 g of an Comparing the produced cumulative amount of butanol and total mixed solvent for the three strains #16, #17 and #18, it was confirmed that strain #16 in which HCB operon or thiolase was not overexpressed showed high ethanol selectivity of 27%, and thus, due to toxicity to the strain, solvent productivity and butanol selectivity were remarkably decreased. On the contrary, in the case of strains #17 and #18 in which hcb operon or atoB were overexpressed respectively, it was confirmed that butanol and solvents were stably produced while maintaining solvent productivity for more than 100 hours of cultivation (Table 11). This means that the process stability was improved during continuous culture, thereby greatly enhancing utility and operation cost.

TABLE 11

| # | fermentation product | | | | yield (%) | productivity (g/L/h) | | ethanol selectivity (%) | butanol selectivity (%) | culture hour (h) | consumed glucose (g) |
|---|---|---|---|---|---|---|---|---|---|---|---|
| | acetone | ethanol | butanol | total ABE | | butanol | ABE | | | | |
| 16 | 26.198 | 216.315 | 367.671 | 804.124 | 35.2 | 2.595 | 2.28 | 27 | 69.80 | 88 | 2281.4 |
| 17 | 16.296 | 161.284 | 1053.327 | 2334.499 | 36.7 | 2.471 | 3.07 | 12 | 80.41 | 101 | 3567.0 |
| 18 | 224.397 | 663.292 | 3337.138 | 4224.847 | 37.4 | 2.425 | 3.07 | 18 | 79.00 | 314 | 12278.3 |

INDUSTRIAL APPLICABILITY

The present invention relates to a recombinant microorganism with improved butanol production ability which has an acetyl-CoA biosynthetic pathway and a butyryl-CoA biosynthetic pathway, wherein a pathway converting acetyl-CoA to acetate is inhibited and a pathway converting acetyl-CoA to butyryl-CoA is promoted. In addition, the present invention relates to a method for producing butanol using the recombinant microorganism.

The invention claimed is:

1. A recombinant microorganism with improved butanol production ability and decreased ethanol production ability in comparison to a wild type microorganism,
    wherein the microorganism is *Clostridium acetobutylicum*,
    wherein a pathway converting acetyl-CoA to acetate is inhibited, a pathway converting acetyl-CoA to butyryl-CoA is promoted, and a pathway converting butyryl-CoA to butyrate is inhibited,
    wherein the pathway converting acetyl-CoA to acetate is a pathway in which acetyl-CoA is converted to acetate by acetate kinase or phosphotransacetylase,
    wherein the pathway converting acetyl-CoA to butyryl-CoA is a pathway in which acetyl-CoA is converted to butyryl-CoA by thiolase or hbd-crt-bcd operon, and
    wherein the pathway converting butyryl-CoA to butyrate is the pathway in which butyryl-CoA is converted to butyrate by butyrate kinase.

2. The recombinant microorganism according to claim 1, wherein butanol production ability is improved in comparison to the wild type microorganism.

3. The recombinant microorganism according to claim 1, wherein the pathway converting acetyl-CoA to acetate is inhibited by inhibiting phosphotransacetylase.

4. The recombinant microorganism according to claim 1, wherein a pathway converting acetyl-CoA to acetoacetyl-CoA is promoted by increasing expression of thiolase or a pathway converting acetoacetyl-CoA to butyryl-CoA is promoted by increasing expression of hbd-crt-bcd operon.

5. The recombinant microorganism according to claim 1, wherein the pathway converting acetyl-CoA to butyryl-CoA is promoted by increasing expression of thiolase or hbd-crt-bcd operon.

6. The recombinant microorganism according to claim 1, wherein a pathway converting butyryl-CoA to butyrate is inhibited by inhibiting butyrate kinase.

7. The recombinant microorganism according to claim 1, wherein a pathway converting acetate to acetyl-CoA or a pathway converting butyrate to butyryl-CoA is promoted by increasing expression of CoA transferase.

8. The recombinant microorganism according to claim 1, wherein a pathway converting butyryl-CoA to butanol is promoted by increasing expression of aldehyde/alcohol dehydrogenase.

9. The recombinant microorganism according to claim 1, wherein a pta which is a gene encoding phosphotransacetylase is deleted or inhibited, and at least one selected from atoB gene encoding thiolase and hbd-crt-bcd operon is introduced or expression thereof is promoted.

10. The recombinant microorganism according to claim 1, wherein ethanol selectivity is 15% or less and butanol selectivity is 70% or more on a batch culture basis.

11. The recombinant microorganism according to claim 1, wherein butanol productivity is 1.0 g/L/h or more on a batch culture basis.

12. The recombinant microorganism according to claim 1, wherein yield is 28% or more.

13. The recombinant microorganism according to claim 1, wherein ethanol selectivity is 15% or less on a fed-batch culture basis.

14. The recombinant microorganism according to claim 1, wherein ethanol selectivity is 20% or less on a continuous culture basis.

15. A method for producing butanol, comprising:
   culturing the recombinant microorganism according to claim 1; and
   recovering butanol from the culture solution.

16. A method for producing butanol, comprising:
   culturing the recombinant microorganism according to claim 2; and
   recovering butanol from the culture solution.

* * * * *